US008300955B2

(12) United States Patent
Nishimura et al.

(10) Patent No.: US 8,300,955 B2
(45) Date of Patent: Oct. 30, 2012

(54) IMAGE PROCESSING DEVICE AND IMAGE PROCESSING METHOD IN IMAGE PROCESSING DEVICE FOR IDENTIFYING FEATURES IN AN IMAGE

(75) Inventors: Hirokazu Nishimura, Hachioji (JP); Tetsuo Nonami, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/168,510

(22) Filed: Jun. 24, 2011

(65) Prior Publication Data

US 2011/0255759 A1    Oct. 20, 2011

Related U.S. Application Data

(62) Division of application No. 11/638,821, filed on Dec. 14, 2006, now abandoned.

(30) Foreign Application Priority Data

Dec. 28, 2005  (JP) ................... 2005-380210
Dec. 28, 2005  (JP) ................... 2005-380212

(51) Int. Cl.
*G06K 9/00*  (2006.01)
*G06K 9/34*  (2006.01)
*G06K 9/38*  (2006.01)
*G06K 9/62*  (2006.01)
*G06K 9/68*  (2006.01)
*G06K 9/70*  (2006.01)
*G06K 9/74*  (2006.01)

(52) U.S. Cl. ........ 382/224; 382/225; 382/226; 382/227; 382/228; 382/128; 382/133; 382/155; 382/156; 382/157; 382/158; 382/159; 382/160; 382/164; 382/165; 382/170; 382/171; 382/172

(58) Field of Classification Search .......... None
See application file for complete search history.

(56) References Cited

U.S. PATENT DOCUMENTS 5,836,872 A    11/1998  Kenet et al.
(Continued)

FOREIGN PATENT DOCUMENTS

EP    0 671 706 A2    9/1995
(Continued)

OTHER PUBLICATIONS

U.S. Official Action dated May 17, 2010 from related application U.S. Appl. No. 11/638,821.

(Continued)

*Primary Examiner* — Tom Y Lu
*Assistant Examiner* — Thomas Conway
(74) *Attorney, Agent, or Firm* — Scully, Scott, Murphy & Presser, P.C.

(57) ABSTRACT

A plurality of images inputted in an image signal input portion are divided into a plurality of regions by an image dividing portion, and a feature value in each of the plurality of regions is calculated by a feature value calculation portion and divided into a plurality of subsets by a subset generation portion. On the other hand, a cluster classifying portion classifies a plurality of clusters generated in a feature space into any one of a plurality of classes on the basis of the feature value and occurrence frequency of the feature value. And a classification criterion calculation portion calculates a criterion of classification for classifying images included in one subset on the basis of a distribution state of the feature value in the feature space of each of the images included in the one subset.

3 Claims, 21 Drawing Sheets

U.S. PATENT DOCUMENTS

| | | | |
|---|---|---|---|
| 6,514,082 B2 * | 2/2003 | Kaufman et al. | 434/262 |
| 6,650,772 B1 * | 11/2003 | Inoue et al. | 382/162 |
| 6,757,412 B1 * | 6/2004 | Parsons et al. | 382/128 |
| 6,996,549 B2 * | 2/2006 | Zhang et al. | 706/16 |
| 7,536,048 B2 * | 5/2009 | Moravec et al. | 382/164 |
| 2002/0102017 A1 | 8/2002 | Kim et al. | |
| 2002/0165837 A1 | 11/2002 | Zhang et al. | |
| 2008/0226148 A1 * | 9/2008 | Gu et al. | 382/128 |

FOREIGN PATENT DOCUMENTS

| | | |
|---|---|---|
| EP | 1 233 374 A2 | 8/2002 |
| JP | 2002-190018 | 7/2002 |
| JP | 2002-329188 | 11/2002 |
| JP | 2005-192880 | 7/2005 |
| WO | WO 98/22909 | 5/1998 |
| WO | WO 99/04690 | 2/1999 |
| WO | WO 02/059828 A2 | 8/2002 |
| WO | WO 02/073507 A2 | 9/2002 |

OTHER PUBLICATIONS

U.S. Official Action dated Feb. 22, 2011 from related application U.S. Appl. No. 11/638,821.

Extended Supplementary European Search Report dated Mar. 25, 2011.

Extended European Search Report dated Mar. 26, 2012 from related EP 11008465.4-2319.

* cited by examiner

IMAGE PROCESSING DEVICE AND IMAGE PROCESSING METHOD IN IMAGE PROCESSING DEVICE FOR IDENTIFYING FEATURES IN AN IMAGE

This application is a divisional application of U.S. application Ser. No. 11/638,821 filed on Dec. 14, 2006, which claims benefit of Japanese Patent Application No. 2005-380210 filed on Dec. 28, 2005, and No. 2005-380212 filed on Dec. 28, 2005, the contents of which are incorporated by reference.

BACKGROUND OF THE INVENTION

1. Field of the Invention

The present invention relates to an image processing device which can exclude images which do not favorably pick up images of the surface of a living mucosa and an image processing method in the image processing device.

2. Description of the Related Art

Observation using image pickup equipment such as X-ray, CT, MRI, ultrasonic observing device, endoscope device and the like has been widely used in the medical field. In such image pickup equipment, the endoscope device, for example, has an elongated insertion portion to be inserted into a body cavity as a living body and has such action and configuration that an image of the inside of the body cavity formed by an objective optical system arranged at a tip end portion of the insertion portion is picked up by an image pickup portion such as a solid-state image sensing device and outputted as an image pickup signal, and the image of the inside of the body cavity is displayed on a display portion such as a monitor based on the image pickup signal. A user observes organs or the like in the body cavity, for example, based on the image of the inside of the body cavity displayed on the display portion such as a monitor. Also, the endoscope device is capable of directly picking up an image of a mucosa of a digestive duct. Therefore, the user can make various observations of color tones of a mucosa, shape of a lesion, fine structure of the surface of a mucosa and so on in a comprehensive manner.

As image pickup equipment for which substantially the same usability as that of the above endoscope device is expected, a capsule-type endoscope device, for example, is proposed. In general, the capsule-type endoscope device comprises a capsule-type endoscope which is arranged in a body cavity by being swallowed by a subject from the mouth and sends a picked-up image of the inside of the body cavity to the outside as an image pickup signal, a receiver for receiving the sent image pickup signal and then, accumulating the received image pickup signals, and an observing device for observing an image of the inside of the body cavity based on the image pickup signal accumulated in the receiver.

Since the capsule-type endoscope constituting the capsule-type endoscope device is advanced by peristalsis of a digestive duct, it generally takes some hours from input into the body cavity through the mouth to ejection from an anus. And since the capsule-type endoscope keeps on outputting an image pickup signal to the receiver during the period from placement in the body cavity to ejection, the number of still images as frame images accumulated in the receiver in moving images for some hours, for example, can be enormous. Thus, in view of more efficient observation by the user, such a proposal is in demand that an image data volume is reduced by processing not to display or store images other than the predetermined images after an image processing method of detecting a predetermined image including a lesion portion such as a bleeding portion is carried out.

The above image processing methods include PCT International Publication No. WO02/073507, for example.

SUMMARY OF THE INVENTION

The image processing device in the present invention comprises an image signal input portion for inputting an image signal based on a plurality of images obtained by medical equipment having an imaging function, an image dividing portion for dividing the plurality of images into a plurality of regions based on the image signal inputted in the image signal input portion, respectively, a feature value calculation portion for calculating one or more feature values in each of the plurality of regions divided by the image dividing portion, a cluster classifying portion for generating a plurality of clusters in a feature space on the basis of the feature value and occurrence frequency of the feature value and for classifying the plurality of clusters into a plurality of classes, a subset generation portion for generating a plurality of subsets on the basis of imaging timing of each of the plurality of images using the plurality of images, and a classification criterion calculation portion for calculating a criterion of classification when classifying the image included in one subset into each of the plurality of classes on the basis of the distribution state of the feature value in the feature space of each image included in the one subset generated by the subset generation portion.

The image processing method in the present invention comprises an image dividing step for dividing an image into each of a plurality of regions on the basis of an image signal inputted on the basis of the image obtained by medical equipment having an imaging function, a feature value calculating step for calculating a feature value in each of the plurality of regions divided by the image dividing step, a cluster classifying step for generating a plurality of clusters in a feature space on the basis of the feature value and occurrence frequency of the feature value and for classifying the plurality of clusters into each of a plurality of classes, a subset generating step for generating a plurality of subsets on the basis of an imaging timing of each of the plurality of images using the plurality of images, and a classification criterion calculating step for calculating a criterion of classification when classifying the image included in one subset on the basis of a distribution state of the feature value in the feature space of each image included in the one subset generated by the subset generation portion.

DESCRIPTION OF THE PREFERRED EMBODIMENTS

Embodiments of the present invention will be described below referring to the attached drawings.

First Embodiment

FIGS. 1 to 18 relates to a first embodiment of the present invention.

Figure 1:
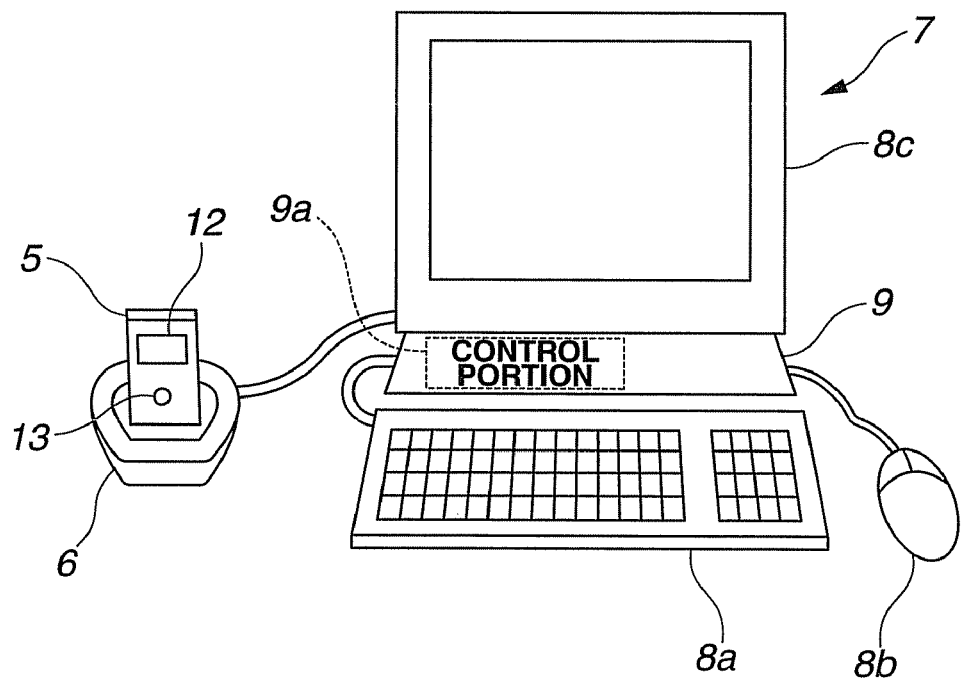
FIG. 1 is an appearance front view showing an appearance of an image processing device and peripheral equipment in which an image processing operation, which is a first embodiment of the present invention is executed.
Figure 2:
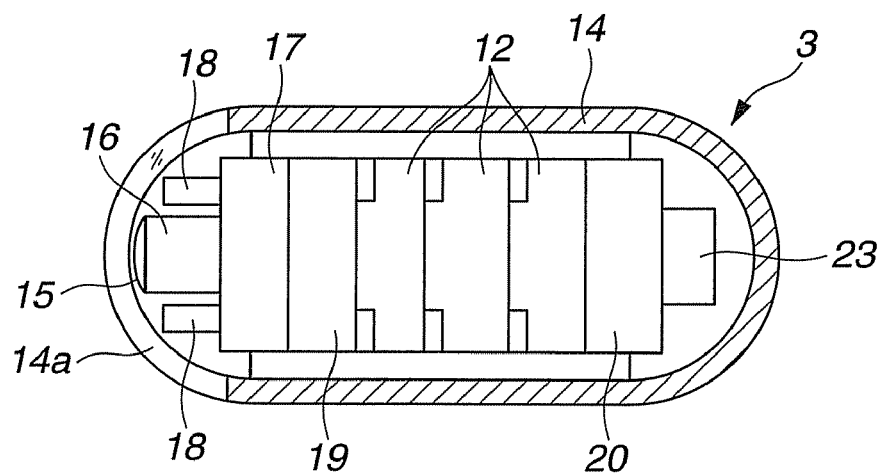
FIG. 2 is an enlarged sectional view of an essential part with a part cut away of a capsule-type endoscope for generating predetermined image information to be processed in the image processing device of the first embodiment.
Figure 3:
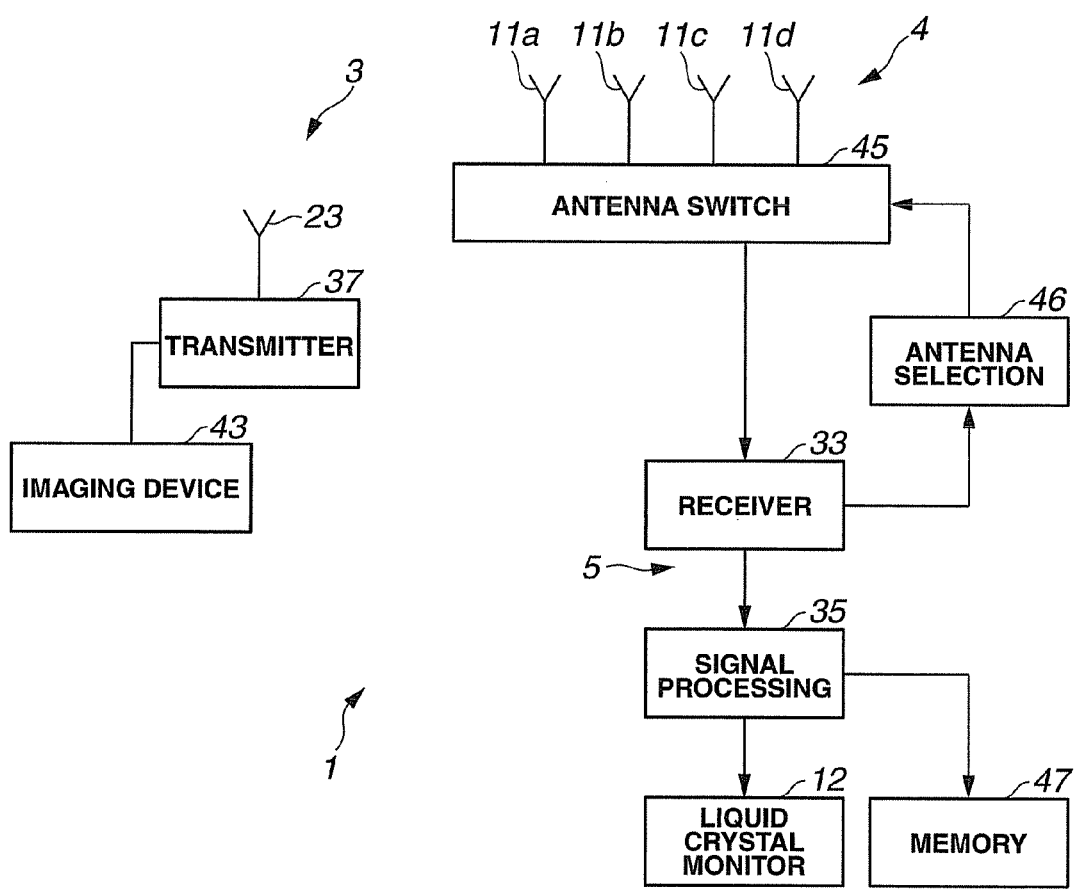
FIG. 3 is a block diagram showing an outline internal configuration of a capsule-type endoscope device supplying the predetermined image information to the image processing device of the first embodiment.
Figure 4:
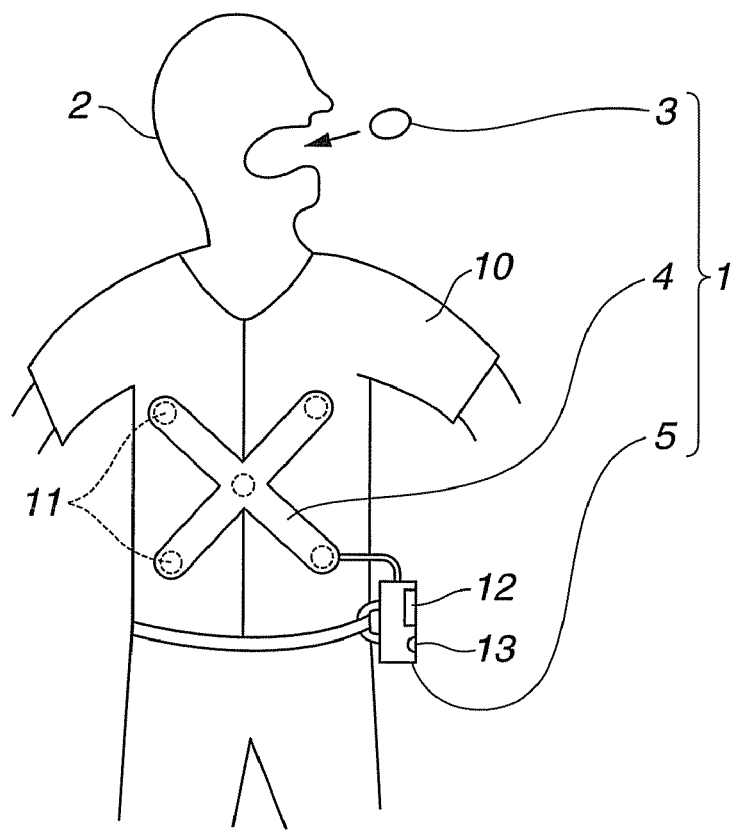
FIG. 4 is a view showing a use example of the capsule-type endoscope device supplying the predetermined image information to the image processing device of the first embodiment.
Figure 5:
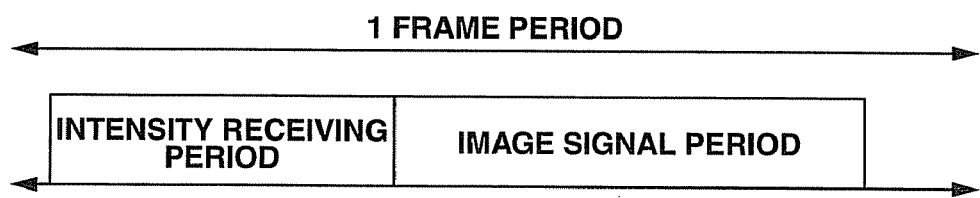
FIG. 5 is a timing chart showing an example of a signal outputted from the capsule-type endoscope shown in FIG. 2.
Figure 6:
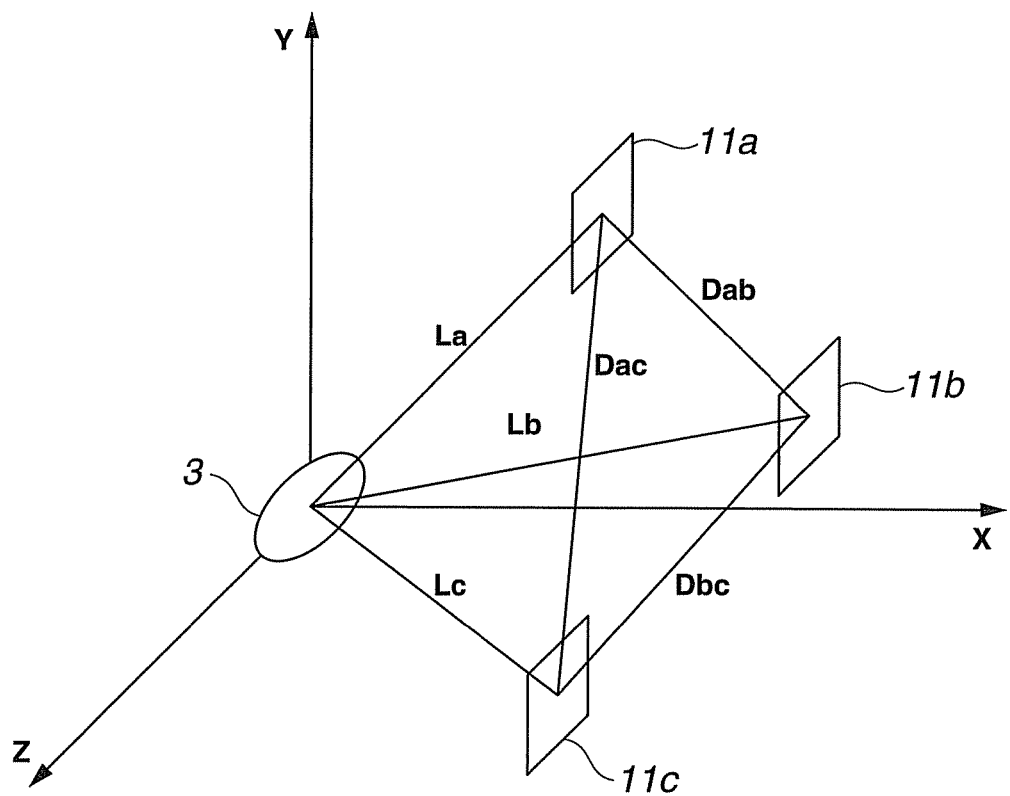
FIG. 6 is an explanatory diagram for explaining position detection of the capsule-type endoscope show in FIG. 2.
Figure 7:
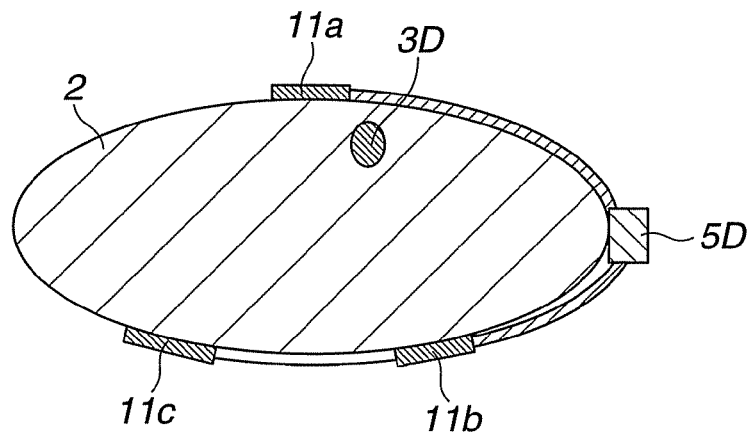
FIG. 7 is an enlarged sectional view of an essential part showing an antenna unit when using the capsule-type endoscope device shown in FIG. 3.
Figure 8:
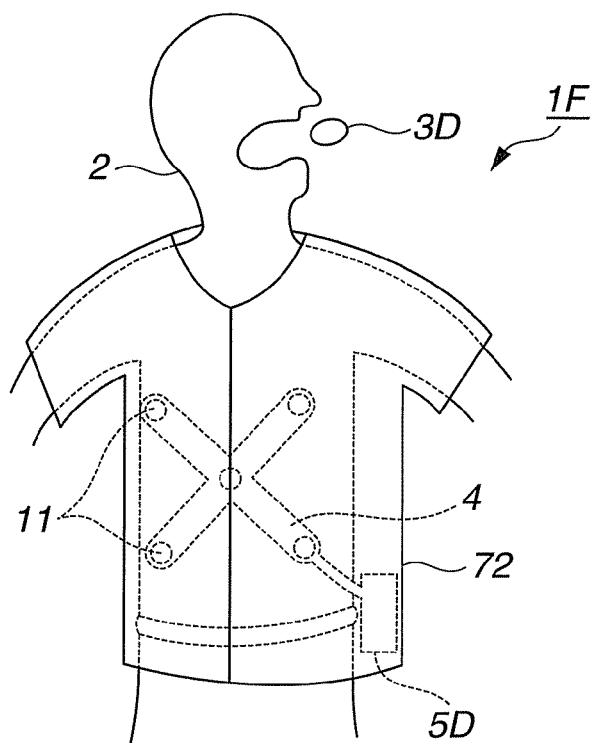
FIG. 8 is an explanatory view for explaining a shield jacket when using the capsule-type endoscope device shown in FIG. 3.
Figure 9:
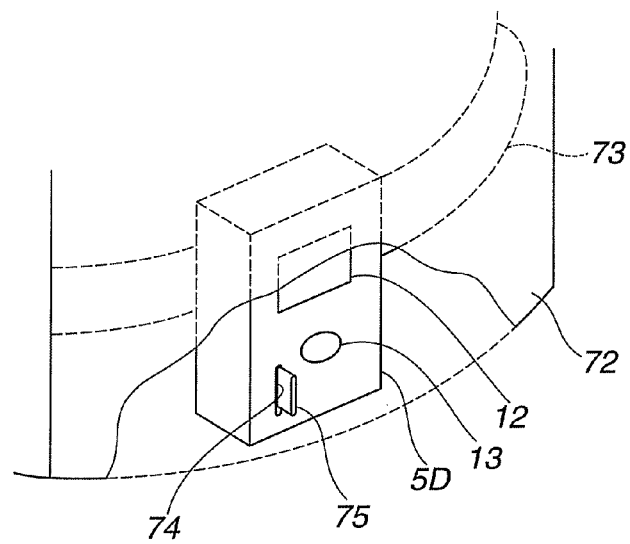
FIG. 9 is an explanatory view for explaining an attached state to a subject of an external device when using the capsule-type endoscope device shown in FIG. 3.
Figure 10:
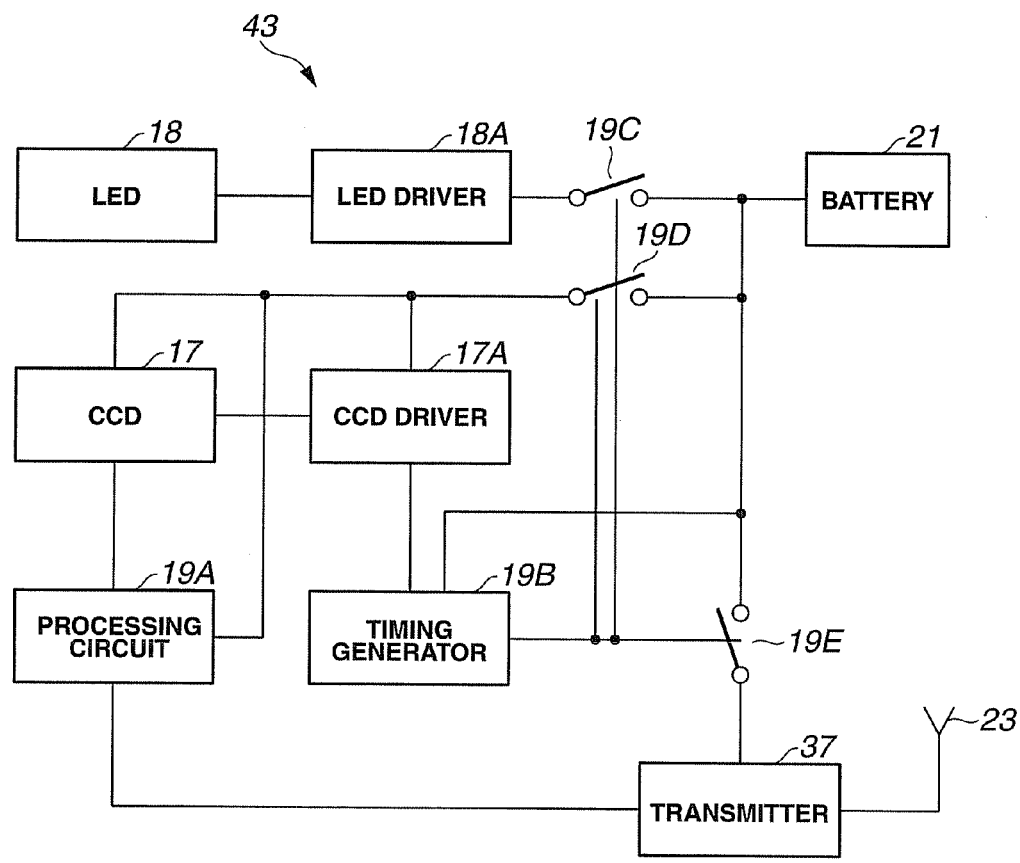
FIG. 10 is a block diagram showing an electrical configuration of the capsule-type endoscope shown in FIG. 2.
Figure 11:
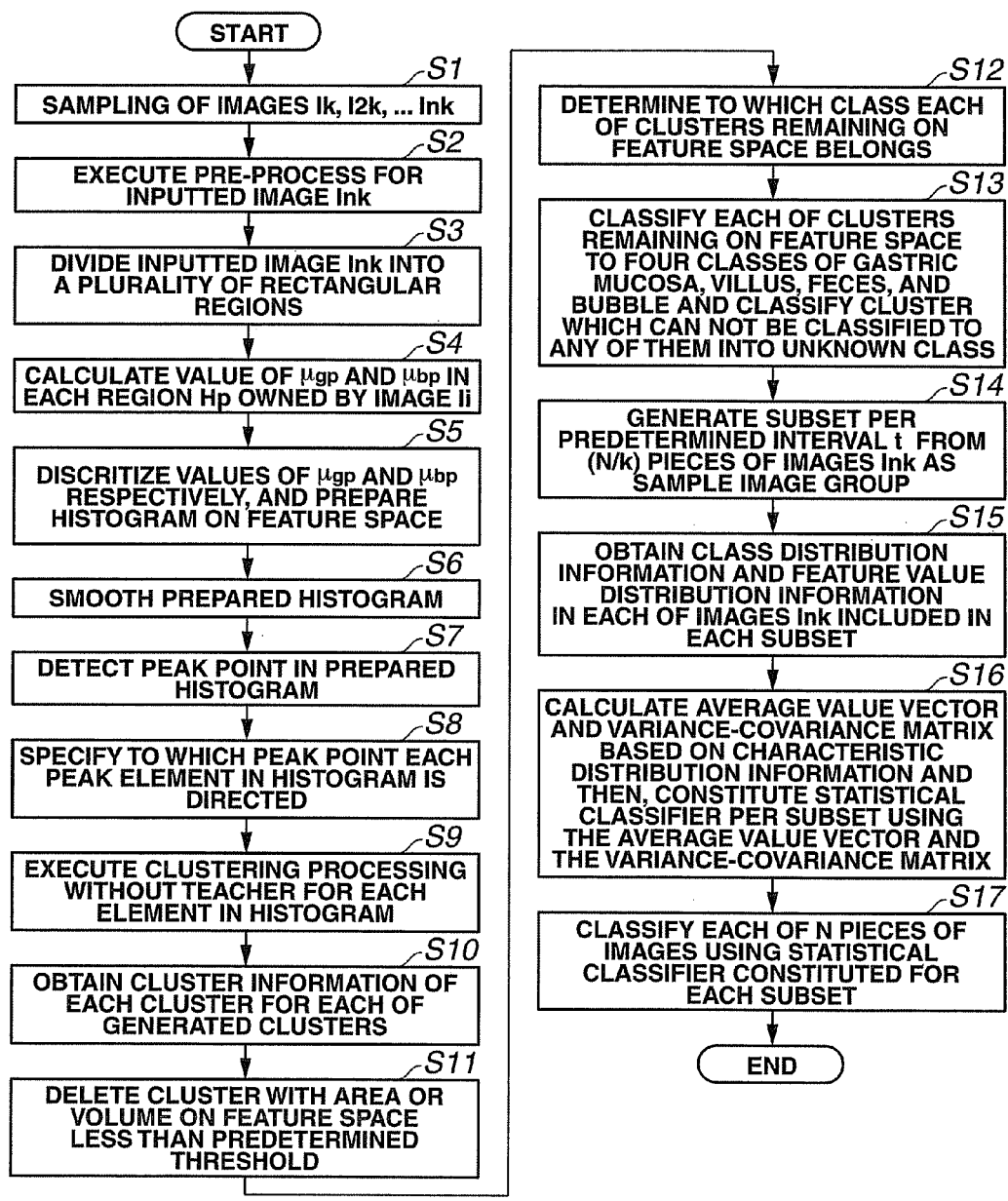
FIG. 11 is a flowchart showing an image processing operation according to the first embodiment.
Figure 12:
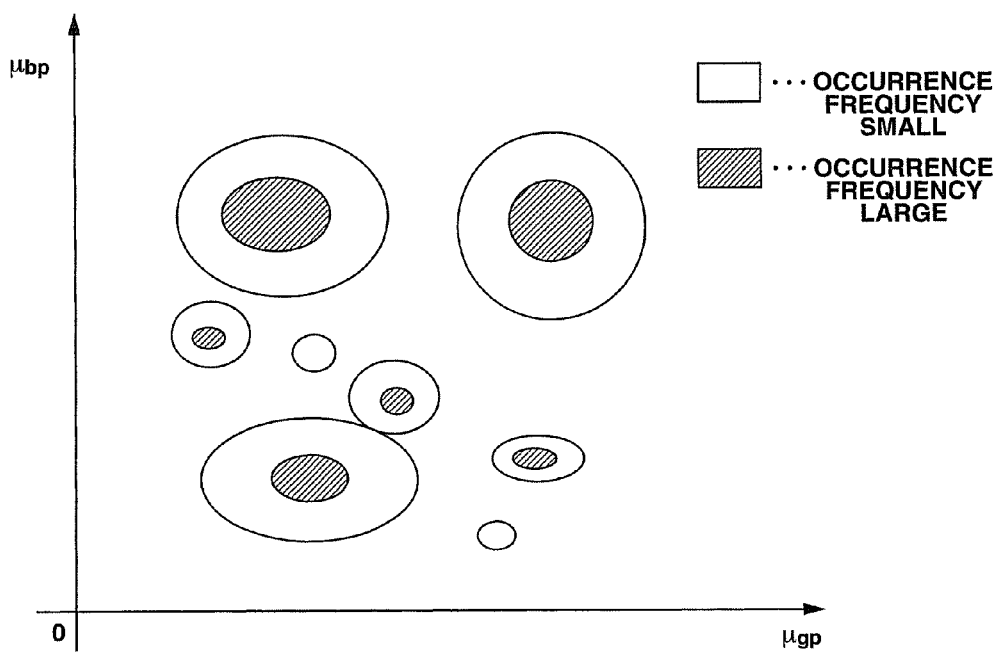
FIG. 12 is a diagram showing an example of a histogram in a feature space generated by processing executed by a control portion.
Figure 13:
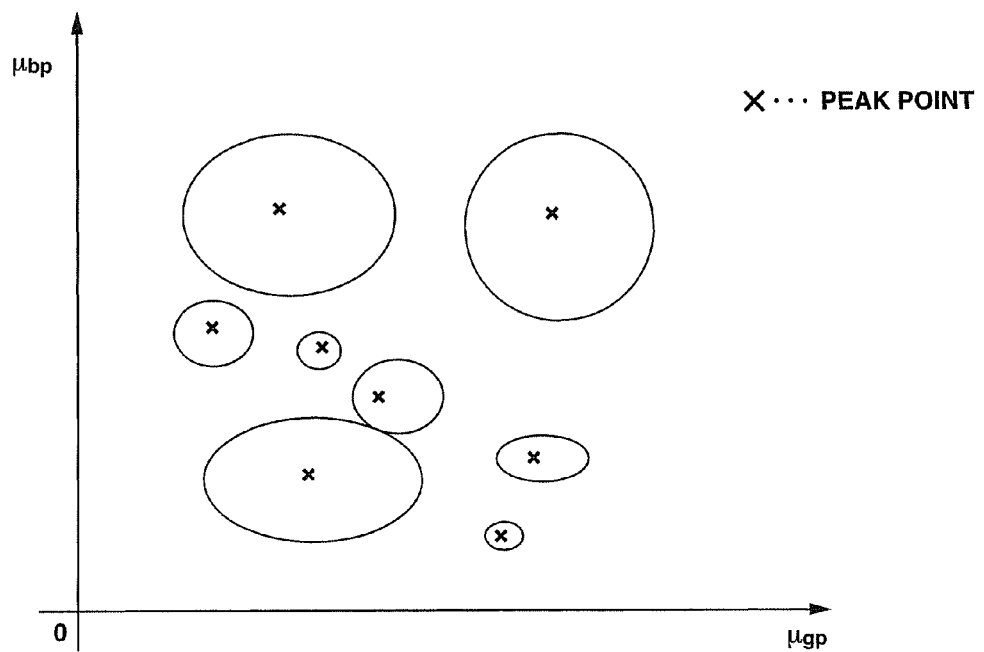
FIG. 13 is a diagram showing an example of clusters in the feature space generated by processing executed by the control portion.
Figure 14:
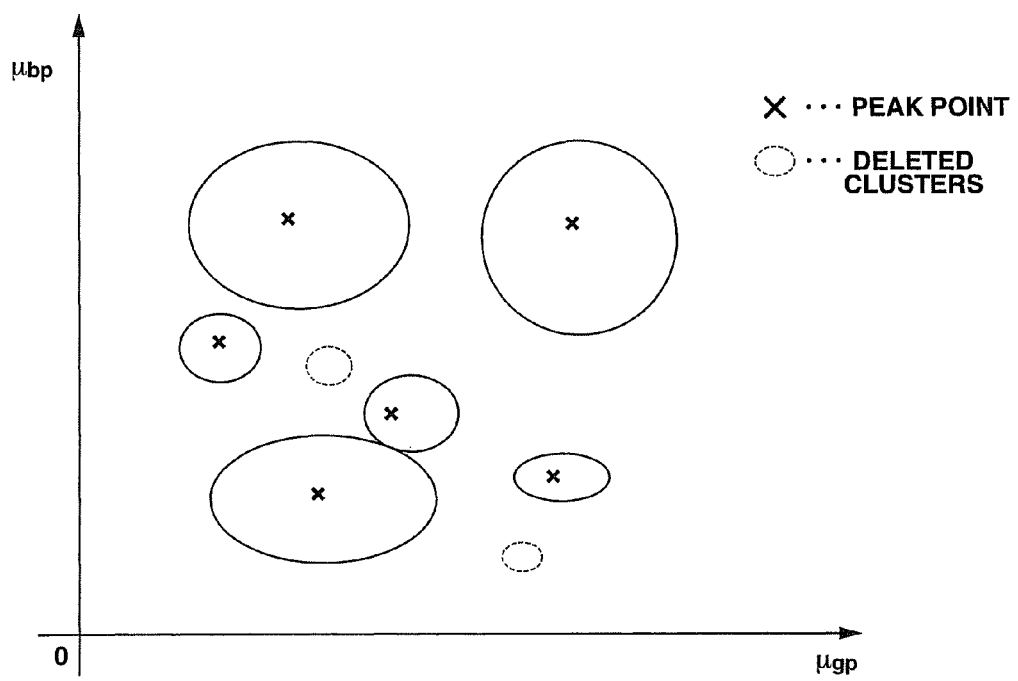
FIG. 14 is a diagram showing a state where a cluster with an area or volume in the feature space less than a threshold value in the clusters shown in FIG. 13 is deleted.
Figure 15:
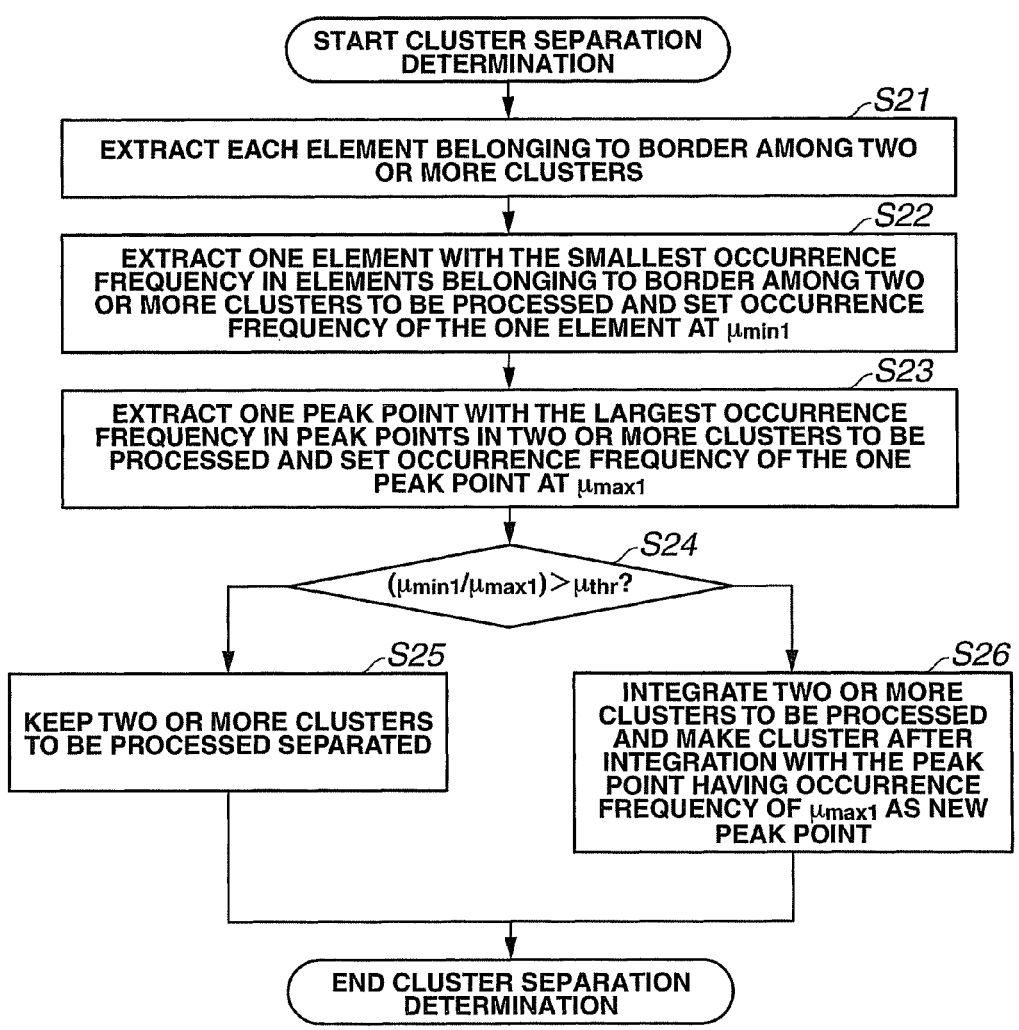
FIG. 15 is a flowchart showing an example of processing for integration or separation determination of two or more bordering clusters, which is processing executed by the control portion.
Figure 16:
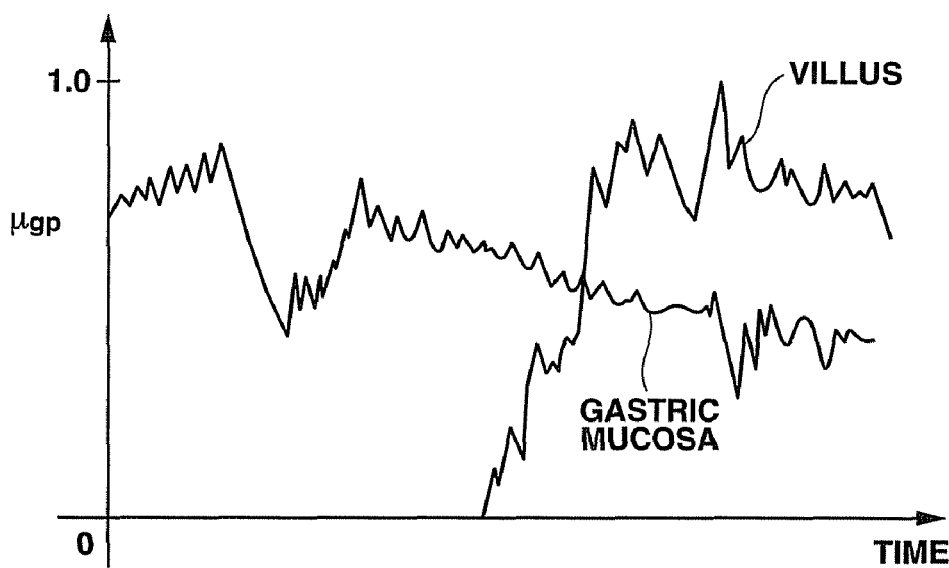
FIG. 16 is a graph showing a change in the time direction per subset of a feature value µgp owned by a region classified into a gastric mucosa class and villus class.
Figure 17:
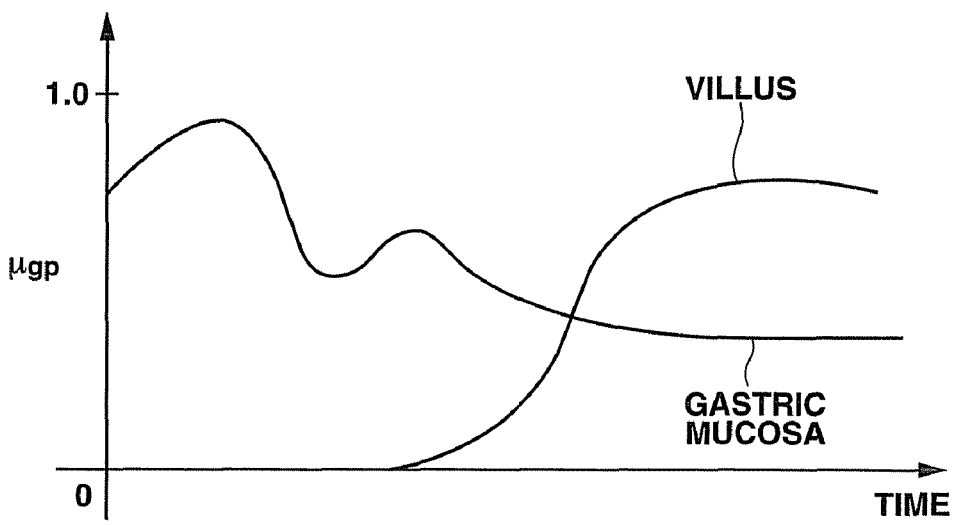
FIG. 17 is a graph when a smoothing processing in the time direction is executed in the feature value µgp shown in the graph in FIG. 16.
Figure 18:
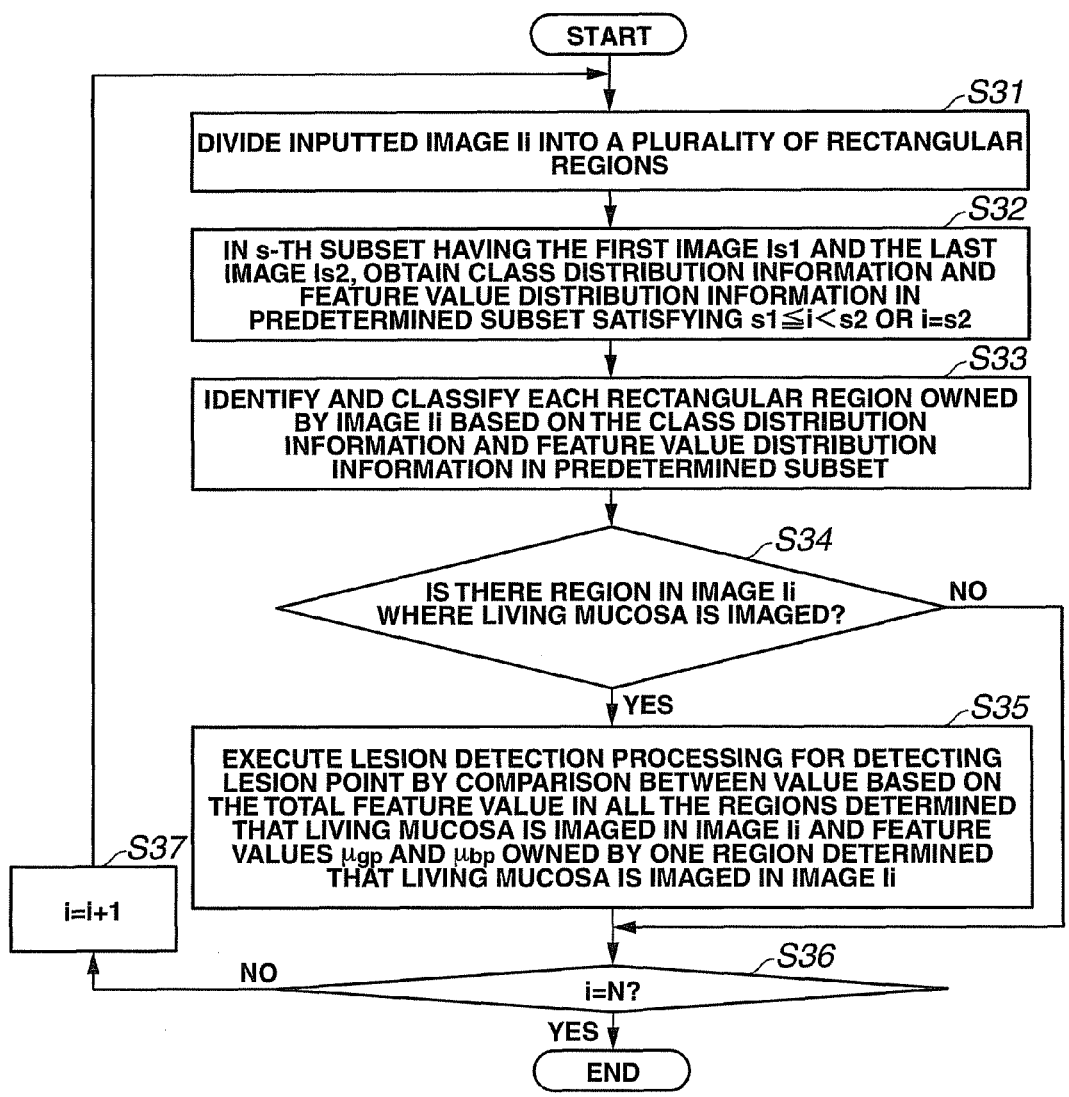
FIG. 18 is a flowchart showing an example of a lesion detection processing, which is processing executed by the control portion.

FIG. 1 is an appearance front view showing an appearance of an image processing device and peripheral equipment in which an image processing operation, which is a first embodiment of the present invention is executed. FIG. 2 is an enlarged sectional view of an essential part with a part cut away of a capsule-type endoscope for generating predetermined image information to be processed in the image processing device of the first embodiment. FIG. 3 is a block diagram showing an outline internal configuration of a capsule-type endoscope device supplying the predetermined image information to the image processing device of the first embodiment. FIG. 4 is a view showing a use example of the capsule-type endoscope device supplying the predetermined image information to the image processing device of the first embodiment. FIG. 5 is a timing chart showing an example of a signal outputted from the capsule-type endoscope shown in FIG. 2. FIG. 6 is an explanatory diagram for explaining position detection of the capsule-type endoscope show in FIG. 2. FIG. 7 is an enlarged sectional view of an essential part showing an antenna unit when using the capsule-type endoscope device shown in FIG. 3. FIG. 8 is an explanatory view for explaining a shield jacket when using the capsule-type endoscope device shown in FIG. 3. FIG. 9 is an explanatory view for explaining an attached state to a subject of an external device when using the capsule-type endoscope device shown in FIG. 3. FIG. 10 is a block diagram showing an electrical configuration of the capsule-type endoscope shown in FIG. 2. FIG. 11 is a flowchart showing an image processing operation according to the first embodiment. FIG. 12 is a diagram showing an example of a histogram in a feature space generated by processing executed by a control portion. FIG. 13 is a diagram showing an example of clusters in the feature space generated by processing executed by the control portion. FIG. 14 is a diagram showing a state where the cluster with an area or volume in the feature space less than a threshold value in the clusters shown in FIG. 13 is deleted. FIG. 15 is a flowchart showing an example of processing for integration or separation determination of two or more bordering clusters, which is processing executed by the control portion. FIG. 16 is a graph showing a change in the time direction per subset of a feature value µgp owned by a region classified into a gastric mucosa class and villus class. FIG. 17 is a graph when a smoothing processing in the time direction is executed in the feature value µgp shown in the graph in FIG. 16. FIG. 18 is a flowchart showing an example of a lesion detection processing, which is processing executed by the control portion.

A capsule-type endoscope device 1 which supplies predetermined image information to an image processing device, which is a first embodiment of the present invention comprises, as shown in FIG. 3, a capsule-type endoscope 3, an antenna unit 4 and an external device 5 as major parts.

The capsule-type endoscope 3 as a medical device is, though the details will be described later, formed into a shape to be arranged in a body cavity by being swallowed from the mouth of a patient 2 as a subject and then, traveling in a digestive duct by a peristaltic motion and is also provided inside with an imaging function for picking up an image of the inside of the body cavity and generating the picked-up image information and a transmitting function for transmitting the picked-up image information to the outside of the body. The antenna unit 4 is, though the details will be described later, arranged on the body surface of the patient 2 and has a plurality of receiving antennas 11 for receiving the picked-up image information transmitted from the capsule-type endoscope 3. The external device 5 has the outer shape formed in a box state, and though the details will be described later, has a function for various processing of the picked-up image information received by the antenna unit 4, recording of the picked-up image information, display of the picked-up image information by the picked-up image information and the like. On the surface of this external device 5, a liquid crystal monitor 12 for displaying the picked-up image and an operation portion 13 for giving an operation instruction of various functions are provided.

This external device 5 has an LED for displaying a warning relating to a remaining amount of a battery for a driving power supply and the operation portion 13 formed from switches such as a power switch provided on the surface of the exterior. Also, in the capsule-type endoscope 3, a calculation execution portion using a CPU and a memory is provided, and it may be configured so that an image processing, which will be described later, is executed for the received and recorded picked-up image information.

This external device 5 is detachably attached to the body of the patient 2 and as shown in FIG. 1, attached to a cradle 6 so that it is detachably connected to an image processing device 7, which is the first embodiment of the present invention (hereinafter referred to as a terminal device). A personal computer is used as this terminal device 7, for example, and it has a terminal body 9 having a processing function and a memory function of various data, a keyboard 8a and a mouse 8b for input of various operation processing, and a display 8c for displaying various processing results. This terminal device 7 takes in the picked-up image information recorded in the external device 5, for example, through the cradle, writes/records it in a rewritable memory built in the terminal body 9 or a portable memory such as a rewritable semiconductor memory which can be detachably attached to the terminal body 9 and has the recorded picked-up image information displayed on the display 8c as a basic function. The picked-up image information recorded in the external device 5 may be taken into the terminal device 7 by a USB cable or the like instead of the cradle 6.

The image processing executed by the terminal device 7 is carried out at a control portion 9a provided at the terminal body 9 as processing to select an image to be displayed according to an elapsed time from the picked-up image information taken in and recorded from the eternal device 5 and an image processing, which will be described later. The control portion 9a has a central processing unit (CPU) and the like and can temporarily hold the processing results in a register or the like, not shown, when executing the above processing.

Next, the outer shape and the internal structure of the capsule-type endoscope 3 will be described using FIG. 2. The capsule-type endoscope 3 has an exterior member 14 with the section in the U shape and a cover member 14a substantially in the semispherical shape formed of a transparent member attached to an open end of the tip end side of the exterior member 14 in the water tight manner by an adhesive. Therefore, the exterior of the capsule-type endoscope 3 is formed so as to have a water-tight structure and a capsule shape when the exterior member 14 and the cover member 14a are connected to each other.

In a portion as an internal hollow portion of the capsule shape having this exterior member 14 and the cover member 14a and located substantially at the center of an arc of the semi-sphere of the cover member 14a, an objective lens 15 for taking in an image of an observed portion inputted through the cover member 14a is stored and arranged in a lens frame 15. At an image forming position of this objective lens 15, a charge coupled device (hereinafter referred to as CCD) 17, which is an image pickup device, is arranged. Also, around the lens frame 16 storing the objective lens 15, four white LED 18 emitting and radiating illumination light are arranged on the same plane (only two LED of them are shown in the figure). In the internal hollow portion of the exterior member 14 at the rear end side of the CCD 17, a processing circuit 19 for generating an image pickup signal photoelectrically converted by drive-control of the CCD 17, an imaging processing to generate a picked-up image signal by applying predetermined signal processing to the image pickup signal, and processing of LED driving for controlling operation of lighting/non-lighting of the LED 18, a communication processing circuit 20 for converting the picked-up image signal generated by the imaging processing of this processing circuit 19 into a wireless signal and sending it, a transmission antenna 23 for transmitting the wireless signal from this communication processing circuit 20 to the outside, and a plurality of button-type batteries 21 for supplying power for driving the processing circuit 19 and the communication processing circuit 20.

The CCD 17, the LED 18, the processing circuit 19, the communication processing circuit 20 and the transmission antenna 23 are arranged on a substrate, not shown, and the substrates are connected to each other by a flexible substrate, not shown. Also, the processing circuit 19 is provided with a calculation circuit, not shown, for executing the image processing, which will be described later. That is, the capsule-type endoscope 3 has, as shown in FIG. 3, an imaging device 43 having the CCD 17, the LED 18 and the processing circuit 19, a transmitter 37 having the communication processing circuit 20, and a transmission antenna 23.

Next, the detailed configuration of the imaging device 43 of the capsule-type endoscope 3 will be described using FIG. 10. The imaging device 43 comprises an LED driver 18A for controlling operation of lighting/non-lighting of the LED 18, a CCD driver 17A for transferring a charge photoelectrically converted by controlling driving of the CCD 17, a processing circuit 19A for generating an image pickup signal using the charge transferred from the CCD 17 and generating a picked-up image signal by applying a predetermined signal processing to the image pickup signal, a switch portion for supplying a driving power from the battery 21 to the LED driver 18A, the CCD driver 17A, the processing circuit 19A, and the transmitter 37, and a timing generator 19B for supplying a timing signal to the switch portion and the CCD driver 17A. The switch portion comprises a switch 19C for turning on/off the power supply from the battery 21 to the LED driver 18A, a switch 19D for turning on/off the power supply to the CCD 17, the CCD driver 17A and the processing circuit 19A, and a switch 19E for turning on/off the power supply to the transmitter 37. Also, to the timing generator 19B, driving power is supplied from the battery 21 all the time.

In the imaging device 43 of the capsule-type endoscope 3 having this configuration, when the switch 19C, the switch 19D and the switch 19E are in the off state, portions other than the timing generator 19B are in the non-operating state. When a timing signal is outputted from the timing generator 19B, the switch 19D is turned on, by which power is supplied from the battery 21 to the CCD 17, the CCD driver 17A and the processing circuit 19A and brought into the operating state.

At the initial driving of the CCD 17, an electronic shutter of the CCD 17 is operated to remove unnecessary dark current and then, the timing generator 19B turns on the switch 19C so as to drive the LED driver 18A to light the LED 18 and have the CCD 17 exposed. The LED 18 is lighted for a predetermined time required for exposure of the CCD 17 and then, turned off at timing when the switch 19C is turned off in order to save power consumption.

The charge accumulated in a predetermined time when the CCD 17 is exposed is transferred to the processing circuit 19A by control of the CCD driver 17A. The processing circuit 19A generates an image pickup signal based on the charge transferred from the CCD 17 and generates an endoscopic image signal by applying a predetermined signal processing to the image pickup signal. When a signal transmitted from the transmitter 37 is an analog wireless method, for example, the processing circuit 19A generates an analog image pickup signal obtained by superimposing a composite synchronizing signal on a CDS output signal and then, outputs the analog image pickup signal to the transmitter 37 as an endoscope image signal. Also, when the signal transmitted from the transmitter 37 is a digital wireless method, the processing circuit 19A generates a digital picked-up image signal obtained by further applying encoding processing such as scramble to a serial digital signal generated by an analog/digital converter and outputs the digital image pickup signal to the transmitter 37 as the endoscope image signal.

This transmitter 37 applies modulation processing to the analog picked-up image signal or digital picked-up image signal, which is the endoscope image signal supplied from the processing circuit 19A and transmits it from the transmission antenna 23 to the outside in the wireless manner. At this time, the switch 19E is turned on/off by the timing generator 19B so that the driving power is supplied to the transmitter 37 only at the timing when the picked-up image signal is outputted from the processing circuit 19A.

The switch 19E may be controlled so that the driving power is supplied to the transmitter 37 after a predetermined time has elapsed since the picked-up image signal is outputted from the processing circuit 19A. Also, the switch 19E may have such a configuration that is controlled to supply power to the transmitter 37 when it is inserted into the body cavity of the patient 2, which is a subject, by a signal outputted from the timing generator 19B based on a detection result of detection of a pH value of a predetermined value by a pH sensor, not shown, detection of a humidity above a predetermined value by a humidity sensor, not shown, detection of a pressure or an acceleration above a predetermined value by a pressure sensor, not shown, or an acceleration sensor, not shown, and the like, provided at the capsule-type endoscope 3.

The imaging device 43 of the capsule-type endoscope 3 usually picks up two images per second (2 frames per second=2 fps), but in case of an inspection of an esophagus, it is possible to pick up 15 to 30 images per second (14 to 30 fps). Specifically, a timer circuit, not shown, is provided at the capsule-type endoscope 3, and driving of the imaging device 43 is controlled by this timer circuit so that high-speed imaging with more picking up images per second is executed within a predetermined time of a timer count and after the predetermined time has elapsed, low-speed imaging with less picking up images per second is used. Alternately, the timer circuit is operated at the same time as power-on of the capsule-type endoscope 3, and the driving of the imaging device 43 may be controlled so that the high-speed imaging is executed by this timer circuit during the time till passage of the esophagus immediately after being swallowed by the patient 2, for example. Moreover, a capsule-type endoscope for low-speed imaging and a capsule-type endoscope for high-speed imaging may be provided separately to be used respectively according to a portion to be observed.

Next, the antenna unit 4 installed on the body surface of the patient 2 will be described. As shown in FIG. 4, in case of an endoscopic inspection by swallowing the capsule-type endoscope 3, the patient 2 wears a jacket 10 on which the antenna unit 4 made of a plurality of receiving antennas 11 are installed. This antenna unit 4 is, as shown in FIG. 7, arranged so that the plurality of receiving antennas 11 having directivity in a single direction such as a patch antenna used in GPS are directed to the direction of inside the body of the patient 2, for example. That is, since a capsule body 3D of the capsule-type endoscope 3 is placed in the body, the plurality of antennas 11 are arranged so as to surround the capsule body 3D in the body. By using this antenna 11 with high directivity, it is hardly affected by interference by an electric wave from other than the capsule body 3D in the body.

The jacket 10 comprises, as shown in FIG. 8, the antenna unit 4 to be placed on the body surface of the patient 2 and a shield jacket 72 formed by an electromagnetic shield fiber covering a body portion 5D of the external device 5 placed at the waist of the patient 2 by a belt. As the electromagnetic shield fiber forming this shield jacket 72, a metal fiber, a metal chemical fiber, a copper sulfide contained fiber or the like is used. This shield jacket 72 is not limited to the jacket shape but may be in the shape of a vest, one-piece suit or the like.

Also, as an example to attach the external device 5 to the shield jacket 72, as shown in FIG. 9, a key hole 74 is provided at the external body 5D of the external device 5 and it is detachably attached to a belt 73 by inserting a key 75 provided at the shield jacket 72 into the key hole 74. Alternately, simply a pocket, not shown, is provided at the shield jacket 72 and the external body 5D is stored in the pocket, or a Velcro tape (registered trademark) is provided at the external body 5D of the external device 5 and the shield jacket 72 so that they are mounted and fixed by the Velcro tape (registered trademark).

That is, by attaching the shield jacket 72 to the body on which the antenna unit 4 is arranged, an electric wave from the outside to the antenna unit 4 is shielded and influence of interference by the outside wave is suppressed.

Next, the configuration of the antenna unit 4 and the external device 5 will be described using FIG. 3. The antenna unit 4 comprises a plurality of antennas 11a to 11d receiving a wireless signal sent from the transmission antenna 23 of the capsule-type endoscope 3 and an antenna switch 45 for switching the antennas 11a to 11d. The external device 5 comprises a receiving circuit 33 for executing receiving processing such as conversion, amplification and the like of the wireless signal from the antenna switch 45 to a picked-up image signal, a signal processing circuit 35 for applying a predetermined signal processing to the picked-up image signal supplied from this receiving circuit 33 so as to generate a signal for displaying a picked-up image and picked-up image data, the liquid crystal monitor 12 for displaying the picked-up image based on a signal for picked-up image display generated by this signal processing circuit 35, a memory 47 for storing picked-up image data generated by the signal processing circuit 35, and an antenna selection circuit 46 for controlling the antenna switch 45 by the size of the wireless signal received/processed by the receiving circuit 33.

The plurality of receiving antennas 11 shown as the receiving antennas 11a to 11d in the figure of the antenna unit 4 receives a wireless signal sent with a given wave intensity from the transmission antenna 23 of the capsule-type endoscope 3. The plurality of receiving antennas 11a to 11d sequentially switch a receiving antenna to receive the wireless signal by control of the antenna switch 45 by an antenna selection signal from the antenna selection circuit 46 of the external device 5. That is, the wireless signal received by each of the receiving antennas 11a to 11d sequentially switched by the antenna switch 45 is outputted to the receiver 33. At this receiver 33, the receiving intensity of the wireless signal of each of the receiving antennas 11a to 11d is detected and the positional relation between each of the receiving antennas 11a to 11d and the capsule-type endoscope 3 is calculated and at the same time, the wireless signal is demodulated and a picked-up image signal is outputted to the signal processing circuit 35. The antenna selection circuit 46 is controlled by output from the receiver 33.

Operation of the antenna switch 45 by the antenna selection circuit 46 will be described. The wireless signal sent from the capsule-type endoscope 3 is, as shown in FIG. 5, supposed to be sent by sequentially repeating a intensity receiving period, which is a period to send a receiving intensity signal indicating the receiving intensity of the wireless signal, and an image signal period, which is a period to send a picked-up image signal in a single-frame transmission period of the picked-up image signal.

To the antenna selection circuit 46, the receiving intensity of the receiving intensity signal received by each of the receiving antennas 11a to 11d is supplied through the receiving circuit 33. The antenna selection circuit 46 compares the intensities of the receiving intensity signals of the antennas 11a to 11d supplied from the receiver 33, determines the optimal receiving antenna to receive the picked-up image signal of the image signal period, that is, an antenna 11i (i=a to d) whose intensity of the receiving intensity signal is the highest and generates and outputs a control signal to switch the antenna switching circuit 45 to that antenna 11i. By this, if the receiving intensity of another antenna is higher than that of the antenna currently receiving an image signal, the receiving antenna of the image signal period is switched at the next frame.

In this way, every time a wireless signal from the capsule-type endoscope 3 is received, the receiving intensity of the picked-up image signal or the receiving intensity signal is compared, and the antenna 11i with the largest receiving intensity is designated as antenna for receiving an image signal by the antenna selection circuit 46 which receives this comparison result. By this, even if the capsule-type endoscope 3 is moved in the body of the patient 2, an image signal obtained from the antenna 11 which can detect a signal with the highest receiving intensity at the moved position can be received. Also, since the moving speed of the capsule-type endoscope 3 is divided into a very slow portion and a rapid portion, an antenna switching operation is not necessarily carried out only once all the time for one image pick-up operation, and the antenna switching operation may be carried out once for a plurality of times of image pick-up operations in the high-speed imaging mode.

Since the capsule type endoscope 3 is moving in the body of the patient 2, it may be so configured that a detection result signal, which is a result of detection of an electric wave intensity, is sent from the external device 5 with an appropriate interval, and the capsule-type endoscope 3 renews its output at transmission based on the signal. In this way, even when the capsule-type endoscope 3 is moved in the body of the patient 2, a transmission output can be set appropriately, wasteful consumption of energy of the battery 21 or the like can be prevented, and the signal transmitting/receiving state can be maintained in an appropriate state.

Next, a method for obtaining information indicating the positional relation between the plurality of receiving antennas 11 and the capsule-type endoscope 3 will be described using FIG. 6. In FIG. 6, a case where the capsule-type endoscope 3 is set at the origin of the three-dimensional coordinates X, Y, Z is described as an example. In order to facilitate the description, three receiving antennas 11a, 11b, 11c among the plurality of receiving antennas 11a to 11d are used, and a distance between the receiving antenna 11a and the receiving antenna 11b is set as Dab, the distance between the receiving antenna 11b and the receiving antenna 11c as Dbc, and the distance between the receiving antenna 11a and the receiving antenna 11c as Dac. Moreover, a predetermined distance relation is set between the receiving antennas 11a to 11c and the capsule-type endoscope 3.

For a wireless signal of a constant sending intensity sent from the capsule-type endoscope 3, a receiving intensity when received by each of receiving antennas $11j$ (j=a, b, c) is a function of a distance Li (i=a, b, c) from the capsule-type endoscope 3 (sending antenna 23 of the capsule-type endoscope 3). Specifically, it depends on the distance Li involving an electric wave damping amount. Therefore, the distance Li between the capsule-type endoscope 3 and each of the receiving antennas $11j$ is calculated from the receiving intensity received by the receiving antenna $11j$ of the wireless signal sent from the capsule-type endoscope 3. For calculation of this distance Li, relational data such as a damping amount of an electric wave by the distance between the capsule-type endoscope 3 and the receiving antenna $11j$ is set at the antenna selection circuit 46, in advance. Also, calculated distance data indicating the positional relation between the capsule-type endoscope 3 and each of the receiving antennas $11j$ is stored in the memory 47 as position information of the capsule-type endoscope 3. The picked-up image information and the position information of the capsule-type endoscope 3 stored in this memory 47 is useful in setting a position for endoscopic observation in an image information processing method by the terminal device 7.

Next, the image processing operation in the image processing device in the first embodiment will be described.

In the first embodiment, an image of the inside of a body cavity picked up by the capsule-type endoscope 3 is comprised by the number of dots in the x-axis direction ISX×the number of dots in the y-axis direction ISY (a value satisfying $1 \leq ISX$, $1 \leq ISY$ and ISX=300, ISY=300, for example), three planes of R (red), G (green), B (blue), and each pixel in each plane takes a value of 8 bits each as an RGB value, which is a density value, that is, a value from 0 to 255. Also, in the first embodiment of the present invention, the i-th image in N pieces of images ($1 \leq N$) picked up continuously in a time series is indicated as Ii ($1 \leq i \leq N$). In the first embodiment, a v-th pixel ($1 \leq v \leq ISX \times ISY$) in each plane of the image Ii is indicated as riv, giv and biv, respectively.

Also, the image processing operation in the image processing device in the first embodiment is carried out as processing in the above-mentioned control portion 9a provided at the terminal body 9 of the terminal device 7.

First, the control portion 9a samples images Ik, I2k, ... Ink (nk is an integer satisfying $1 \leq nk \leq N$) at every k-th image in N pieces of images picked up continuously in a time series by the capsule-type endoscope 3 based on a sampling value k (k=1, 2, ...) set in advance at the terminal device 7 (Step S1 in FIG. 11). When the capsule-type endoscope 3 picks up two images per second and the sampling value k is set to 20, for example, the control portion 9a samples one image per 10 seconds elapsed after the imaging start time in N pieces of images picked up by the capsule-type endoscope 3.

And the control portion 9a groups the sampled (N/k) pieces (N/k is an integer with fractions rounded off) of the images Ink as a sample image group and then, carries out the following processing to each of the images Ink of the sample image group. The sample image group may consist of (n+1) pieces of images including the first image I1 in addition to the (N/k) pieces of images Ink.

At the control portion 9a, noise elimination by median filtering and inverse γ correction, for example, are carried out as pre-process for each plane of Rnk, Gnk and Bnk constituting the inputted image Ink and at the same time, in order to eliminate a halation pixel and a dark part pixel from the subsequent processing targets, they are detected by processing based on a threshold value (Step S2 in FIG. 11). The processing based on the threshold value is carried out as processing to determine as the dark part pixel if all the density values of rnkv, gnkv and bnkv are 10 or less or as the halation pixel if all the density values of rnkv, gnkv and bnkv are 230 or more, for example.

The control portion 9a divides the inputted image Ink into a plurality of rectangular regions consisting of 8×8, for example (Step S3 in FIG. 11). In the subsequent description, one region in the rectangular regions divided at the control portion 9a is indicated as Hp (p is an integer of 1 or more).

Then, the control portion 9a calculates two feature values indicating chromaticity of the image, which are values based on a ratio of the RGB value of each pixel in each region Hp of the image Ink and made of an average value of gnkv/rnkv (hereinafter referred to as μgp) and an average value of bnkv/gnkv (hereinafter referred to as μbp) (Step S4 in FIG. 11).

Moreover, the control portion 9a discretizes the feature values μgp and μbp obtained in each of the regions Hp, respectively, and prepares a histogram in a feature space based on the occurrence frequency of the discretized feature values μgp and μbp (Step S5 in FIG. 11). Specifically, the control portion 9a makes all the values of μgp and μbp at 1 or more as 1 and handles them as they take values from 0 to 1, respectively, and moreover, values obtained by multiplying the feature values μgp and μbp as the values from 0 to 1 by 80 are rounded off to integer values and discretization and creation of a histogram are performed.

The control portion 9a applies an average-value filter of a predetermined size, for example, to the discretized feature values μgp and μbp so as to smooth the histogram (Step S6 in FIG. 11). The histogram prepared by the above processing of the control portion 9a is as shown in FIG. 12, for example.

Next, in the histogram prepared by executing the above-mentioned processing for all the (N/k) pieces of images as the sample image group, the control portion 9a detects an element with the maximum occurrence frequency (μgp, μbp), that is, a peak point (Step S7 in FIG. 11). Specifically, the control portion 9a extracts nine elements consisting of one element and eight elements neighboring the one element in the prepared histogram and then, detects the element with the largest occurrence frequency as the peak point in the extracted nine elements.

The control portion 9a specifies to which peak point among the detected peak points each element other than (μgp, μbp) =(0, 0) is directed in the prepared histogram by using a Valley-Seeking method, for example, as an analysis method on the basis of a gradient vector (Step S8 in FIG. 11). And the control portion 9a carries out clustering processing without a teacher for each element in the histogram, which is processing to consider the elements having the gradient vector directed to the same peak point as elements belonging to the same cluster (Step S9 in FIG. 11). Each cluster prepared by the clustering processing without a teacher by the control portion 9a is as shown in FIG. 13, for example.

If the control portion 9a detects that two or more clusters are bordered in the above clustering processing without a teacher, it may further carry out processing of integration or separation determination of the two or more clusters as described below.

In that case, it is determined that the two or more clusters are bordered by extracting the element including two or more clusters in the nine elements including the eight neighboring elements in each prepared cluster, that is, by extracting the elements belonging to the border of two or more clusters (Step S21 in FIG. 15). Moreover, the control portion 9a extracts one element with the smallest occurrence frequency in the elements belonging to the border of the two or more clusters to be processed and sets the occurrence frequency in the one element as μmin1 (Step S22 in FIG. 15). Also, the control portion 9a extracts one peak point with the largest occurrence frequency in the peak points in the two or more clusters to be processed and sets the occurrence frequency in the one peak point as μmax1 (Step S23 in FIG. 15).

After extracting μmin1 and μmax1, the control portion 9a compares the value of μmin1/μmax1 and a threshold value μthr. When the control portion 9a detects that the value of μmin1/μmax1 is larger than the threshold value μthr (Step S24 in FIG. 15), the two or more clusters to be processed are determined as separate clusters and the two or more clusters are kept separated (Step S25 in FIG. 15). Also, when the control portion 9a detects that the value of μmin1/μmax1 is smaller than the threshold value μthr (Step S24 in FIG. 15), it is determined that the two or more clusters to be processed belong to the same cluster and the two or more clusters are integrated and a cluster after integration with the peak point of the occurrence frequency μmax1 made as a new peak point is prepared (Step S26 in FIG. 15). The above threshold value μthr is 0.1, for example, in the first embodiment.

After the above clustering processing without a teacher (processing shown at step S9 in FIG. 11), the control portion 9a obtains cluster information of each cluster for each generated cluster (Step S10 in FIG. 11). The cluster information obtained by the control portion 9a is information such as a cluster number, an element to be the peak point of each cluster, an area and a volume of each cluster in the feature space, an average value vector of the feature values μgp and μbp in each cluster, for example.

After that, the control portion 9a deletes the clusters with the area or volume in the feature space less than a predetermined threshold value on the basis of the obtained cluster information as shown in FIG. 14 (Step S11 in FIG. 11).

Moreover, by using a classifier of linear discrimination function or function based on Bayes' theorem, for example, prepared from the average value vector of the feature values μgp and μbp in each cluster remaining in the feature space and a training data set, the control portion 9a determines to which class each cluster remaining in the feature space belongs (Step S12 in FIG. 11). In the first embodiment, they shall be four classes consisting of gastric mucosa, villus, feces and bubble. Also, in the first embodiment, the training data set shall be a plurality of images constituting training data of the four classes.

The control portion 9a classifies each cluster remaining in the feature space to the four classes of gastric mucosa, villus, feces and bubble and classifies a cluster which can not be classified into any of the four classes into an unknown class (Step S13 in FIG. 11).

A specific example of processing shown in Step S12 and step S13 in FIG. 11 will be described below in detail. The control portion 9a is supposed to carry out each of the processing described below for all the clusters remaining in the feature space.

In the identification and classification of the above four classes, a prior probability that one class ωa (a=1, 2, ..., C, C indicates the class number) occurs is set as P(ωa), a characteristic vector determined from the feature values μgp and μbp in each cluster remaining in the feature space as x, a probability density function on the basis of the occurrence probability of the characteristic vector x from all the classes as p(x), and a conditional probability density (multivariate normal probability density) function on the basis of an occurrence probability of the characteristic vector x from the one class ωa as p(x|ωa), a calculation formula to calculate a posterior probability P(ωa|x) that an occurring characteristic vector x belongs to one class ωa is shown as the following expression (1):

$$P(\omega a|x) = p(x|\omega a)P(\omega a)/p(x) \quad (1)$$

The conditional probability density function p(x|ωa) and the probability density function p(x) are shown by the following equation (2) and equation (3):

$$p(\underline{x}|\omega a) = (1/((2\pi)^{d/2}|\Sigma a|^{1/2}))\exp[(-1/2)(\underline{x}-\underline{\mu a})^t \Sigma a^{-1}(\underline{x}-\underline{\mu a})] \quad (2)$$

$$p(\underline{x}) = \sum_{a=1}^{C} p(\underline{x}|\omega a)P(\omega a) \quad (3)$$

In the above equations (2) and (3), d indicates the number of dimensions in the same number as that of the feature values of x, μa and Σa indicate an average vector of the characteristic vector x in the class ωa and a variance-covariance matrix in the one class ωa. Also, (x−μa)$^t$ indicates a transposed matrix of (x−μa), |Σa| indicates a determinant of Σa, and Σa$^{-1}$ indicates an inverse matrix of Σa. Moreover, in order to facilitate the description, the prior probability P(ωa) is presumed to take an equal value in all the classes, and the probability density function p(x) is expressed by the above equation (3) as a function common to all the classes.

Together with the statistical classifier on the basis of the above-mentioned Bays' theorem, the average vector μa and the variance-covariance matrix Σa are elements constituting a population parameter in one class ωa, and at the stage before the first image I1 is inputted into the terminal device 7, it is calculated for each class in advance from the characteristic vector x determined every time in each of the regions of the image on the basis of a plurality of images constituting the training data of the four classes consisting of gastric mucosa, villus, feces and bubble and then, recorded in the terminal device 7 as an initial value, respectively. At this time, the control portion 9a may estimate the parameter by adding the characteristic vector of each class in the image Ii to the characteristic vector in the training data of each class.

The average vector μa is comprised by average values of the two feature values owned by the characteristic vector x and is a vector having the same number of dimensions as that of the characteristic vector x. That is, when the characteristic vector x is represented as x=(μgp, μbp), the average vector μa shall be represented as μa=(μ(μgp), μ(μbp)) using μ(μgp) and μ(μbp), which are average values of the two feature values owned by the characteristic vector x, respectively. Also, the variance-covariance matrix Σa is a matrix indicating variation and wideness of distribution of the characteristic vector x belonging to one class ωa and is represented as d×d matrix to the number of dimensions d, which is equal to the number of feature values of the characteristic vector x.

The control portion 9a calculates the posterior probability P(ω1|x) that an occurring characteristic vector x belongs to a class ω1, the posterior probability P(ω2|x) that the occurring characteristic vector x belongs to a class ω2, the posterior probability P(ω3|x) that the occurring characteristic vector x belongs to a class ω3, and the posterior probability P(ω4|x) that the occurring characteristic vector x belongs to a class ω4, respectively, using the equations (1) to (3) on the basis of Bays' theorem. And the control portion 9a identifies that characteristic vector x belongs to the class ωa giving the largest posterior probability P1(ωa|x), classifies one cluster where the characteristic vector x occurred into the class ωa on the basis of the identification result and calculates a value of the probability density function p1(x|ωa) giving the largest posterior probability P1(ωa|x).

In order to determine if the classification result of the one cluster classified into the class ωa is accurate or not in the processing so far, the control portion 9a further executes processing on the basis of the distance from the average value, that is, processing on the basis of the threshold value to the value of the probability density function p1(x|ωa) giving the largest posterior probability P1(ωa|x).

Specifically, first, in the average value of each of the two feature values owned by the average vector μa, for the average value μ(μgp) of the feature value μgp, for example, the threshold vector xb1 including a value to which a product of the standard deviation σ(μgp) of the feature value μgp and a multiplier coefficient α as a predetermined constant is added is determined This threshold vector xb1 is expressed as the following equation (4), for example, and in the first embodiment, the value of the multiplier coefficient α shall be 1.5:

$$xb1=(\mu(\mu gp)+\alpha\times\sigma(\mu gp),\mu bp) \quad (4)$$

When the threshold vector xb1 is determined by the above equation (4), the control portion 9a substitutes the threshold vector xb1 for x of the above equation (1), the equation (2) and the equation (3) so as to calculate the value of the probability density function p(xb1|ωa) as a threshold value of the class ωa to which one cluster is classified.

When the control portion 9a detects that the value of p1(x|ωa) is larger than the value of p(xb1|ωa), it determines that the classification result that the one cluster is classified into the class ωa in the above processing is accurate.

On the other hand, when the control portion 9a detects that the value of p1(x|ωa) is smaller than the value of p(xb1|ωa), it determines that the classification result that the one cluster is classified into the class ωa in the above processing is not accurate, and the one cluster is classified into an unknown class.

Moreover, after the above classification, the control portion 9a generates subsets per predetermined interval t on the basis of the imaging timing from the (N/k) pieces of images Ink as the sample image group (Step S14 in FIG. 11). When images every 10 seconds from the imaging start time are sampled one by one (k=20 is set) and the interval t is set to 180, the control portion 9a makes a subset of images included in the (N/k) pieces of images Ink till 1800 seconds have elapsed since the imaging start time as the sample image group.

After that, the control portion 9a obtains class distribution information indicating distribution of the type of classes occurring in the feature space and feature-value distribution information indicating the distribution state per class of the feature values μgp and μbp included in the cluster occurring in the feature space (Step S15 in FIG. 11). Then, after calculating the average value vector and the variance-covariance matrix as criteria of classification when classifying images on the basis of the above feature-value distribution information, the control portion 9a constitutes a classifier per subset using the average value vector and the variance-covariance matrix (Step S16 in FIG. 16). Moreover, the control portion 9a classifies each of N pieces of images using the classifier per subset constituted by the above processing (Step S17 in FIG. 11). By the above processing, the parameter of the multivariate normal probability density function to specify distribution of each class can be optimally set for each subset in the above statistical classifier.

The control portion 9a can classify images picked up by the capsule-type endoscope 3 with high accuracy and at high speed by executing the processing shown at Step S1 in FIG. 11 to Step S17 in FIG. 11 as mentioned above.

The control portion 9a does not have to calculate the average value vector and variance-covariance matrix for the class not occurring in one subset on the basis of the obtained feature value distribution information.

The above processing executed by the control portion 9a is not limited to be executed after picking up of N pieces of images but may be carried out immediately after images of one subset are picked up based on the interval t or as appropriate, for example.

Moreover, the control portion 9a may execute smoothing processing, which is processing using a smoothing filter with a predetermined size evenly weighted in one dimension, for example, for the feature value distribution information obtained in the processing shown in Step S15 in FIG. 11 in order to obtain processing results with higher accuracy. And the control portion 9a can specify the imaged portion or lesion portion from the portion with remarkable fluctuation of the feature value μgp or μbp or the maximum fluctuation of the feature value μgp or μbp in the feature value distribution information by carrying out the smoothing processing as above.

An example of a method for specifying the imaged portion and the lesion portion by the control portion 9a on the basis of the processing result of the above smoothing processing will be described below.

When a change in the time direction per subset of the feature value μgp owned by the region classified into the gastric mucosa class and the villus class is indicated on the basis of the feature value distribution information obtained by the control portion 9a in the processing shown in Step S15 in FIG. 11, for example, the change is shown as the graph in FIG. 16.

If the same imaged portion is continuously imaged, the color tone of a living mucosa or the like does not originally involve frequent fluctuation in the time direction. Therefore, the values of the feature values μgp (or the feature value μbp) obtained from the images close to each other in terms of time are considered to take similar values.

And as a filter with a predetermined size set in advance on the basis of the above viewpoint, by smoothing processing, using a filter of size 20 evenly weighted in one dimension, by the control portion 9a in the time direction to the feature value μgp shown in a graph as in FIG. 16, the change in the time direction for each subset of the feature value μgp is shown in a graph as in FIG. 17. The graphs shown in FIGS. 16 and 17 show the change in the time direction of the feature value μgp in each subset but it is also possible to draw substantially the same graph showing a change in the time direction for each subset in the feature value μbp.

When the control portion 9a detects that a time zone when the value of the feature value μgp or feature value μbp is remarkably fluctuated exists even after the smoothing processing, it determines that a change of an imaged portion is confirmed in the time zone, for example. Alternately, when the control portion 9a detects that a time zone when the value of the feature value μgp or feature value μbp is remarkably fluctuated exists even after the smoothing processing, it determines that presence of feces, bubble of bile, a lesion portion or the like is confirmed in the time zone, for example.

When the capsule-type endoscope 3 is moved from the stomach to the small intestine (duodenum), for example, digestive juice such as bile is secreted, by which a yellowish image of the subject is taken. Thus, when the control portion 9a detects the presence of the time zone when the value of the feature value μbp in the gastric mucosa class and the villus class shows a remarkable drop, a change of the imaged portion of the capsule-type endoscope 3 from the stomach to the small intestine in the time zone can be identified.

Also, if the capsule-type endoscope 3 passes through a bleeding portion as one of lesion portions, for example, a reddish image of the subject is taken due to the presence of blood at the bleeding portion. Thus, when the control portion 9a detects the presence of the time zone when the value of the feature value μgp in the same class shows a remarkable drop, imaging of the lesion portion by the capsule-type endoscope 3 can be identified.

The control portion 9a may execute the following processing in addition to a series of the above processing shown from Step S1 in FIG. 11 to Step S17 in FIG. 11. In the following processing, class distribution information obtained by the control portion 9a includes five types of class information of gastric mucosa, villus, feces, bubble, and unknown. Also, the above class distribution information is not limited to that including information of the above five classes but it may include information that the gastric mucosa and the villus classes are handled as the same class of a living mucosa class and the feces, bubble and unknown classes are handled as the same class of a non-living mucosa class. Also, it may include information that white-tone living mucosa and yellow-tone living mucosa are handled as the same class.

The control portion 9a carries out the above processing at step S17 in FIG. 11 and then, divides the inputted i-th image Ii into a plurality of rectangular regions of 8×8, for example (Step S31 in FIG. 18).

Here, supposing that the first image and the last image owned by the s-th (s is an integer) subset generated in the above processing up to Step S17 in FIG. 11 are Is1 and Is2, respectively (s1 and s2 are integers satisfying $1 \leq s1 < s2 \leq N$), the control portion 9a obtains class distribution information and feature value distribution information in a predetermined subset satisfying $s1 \leq i < s2$ or i=s2 (Step S32 in FIG. 18).

After that, the control portion 9a identifies to which class of the five classes consisting of gastric mucosa, villus, feces, bubble and unknown each rectangular region owned by the image Ii belongs is identified on the basis of the class distribution information and feature value distribution information in a predetermined subset satisfying $s1 \leq i < s2$ or $i=s2$, and classification based on the identification result is made (Step S33 in FIG. 18). The control portion 9a may identify and classify the class not occurring in the above processing up to step S17 in FIG. 11 using the feature value distribution information estimated in advance based on the training data.

Moreover, the control portion 9a determines if a region classified as gastric mucosa or villus, that is, a region where a living mucosa is imaged exists in each of the rectangular regions of the image Ii on the basis of the classification result at Step S33 in FIG. 18. And when the region where the living mucosa is imaged exists in the rectangular regions of the image Ii (Step S34 in FIG. 18), the control portion 9a executes processing to detect a lesion spot, that is, processing to detect bleeding or redness, for example, as lesion detection processing by comparing a value based on the total feature value in all the regions determined that the living mucosa is imaged in the image Ii and values of the feature values μgp and μbp owned by one region determined that the living mucosa is imaged in the image Ii (Step S35 in FIG. 18).

Specifically, on the basis of the values of the feature values μgp and μbp owned by the one region determined that the living mucosa is imaged in the image Ii and an average value of giv/riv (hereinafter referred to as μgi) and an average value of biv/giv (hereinafter referred to as μbi) as values based on a ratio of the RGB value of each pixel included in all the regions determined that the living mucosa is imaged in the image Ii, by comparing μgp and μgi and comparing μbp and μbi, the control portion 9a detects a region where bleeding or redness is imaged in the regions where the living mucosa is imaged in the image Ii. By this processing, the control portion 9a can accurately detect one region having chromaticity determined to present bleeding or a change in redness as a bleeding region or a redness region against average chromaticity of all the regions determined that the living mucosa is imaged in the region division result involving classification. It may be so constituted that the control portion 9a can detect a region where bleeding or redness is imaged for the region classified as the unknown class in the image Ii by further executing processing on the basis of the comparison result of the feature values owned by the one region classified as the unknown class in the image Ii and μgi as well as μbi in addition to the region where the living mucosa is imaged in the image Ii.

When the above processing has not been completed for all the N pieces of inputted images (Step S36 in FIG. 18), the control portion 9a adds 1 to the image number i (Step S37 in FIG. 18) and continually carries out processing from Step S31 to step S36 in FIG. 18 for the subsequent image.

The control portion 9a may determine that villus in yellow tone due to bile or the like is also a region where the living mucosa is imaged in addition to the regions classified as gastric mucosa or villus.

The above image processing method is not limited to be applied only to an image picked up by the capsule-type endoscope but may be applied to an image picked up by an endoscope which can be inserted into a living body and comprises an insertion portion having an imaging function.

As mentioned above, according to the image processing method in the first embodiment, images can be classified with accuracy and at high speed for each target to be imaged and moreover, an imaged organ can be identified on the basis of the classification result. As a result, observation effects by users can be improved.

Also, according to the first embodiment, by further using the above lesion detection processing for each region classified as a region where the living mucosa is imaged, detection accuracy of a lesion portion can be improved.

In the first embodiment, description was made that the control portion 9a carries out a series of processing by dividing one image Ii into a plurality of rectangular regions with the size of 8×8, but not limited to this, processing may be executed by dividing it into 1×1, that is, per pixel or by dividing it into rectangular regions with another size.

Moreover, in the first embodiment, description was made that the control portion 9a carries out a series of processing by dividing one image Ii into a plurality of rectangular regions with the size of 8×8, but not limited to this, processing may be executed by dividing into regions on the basis of the classification result in one image Ii according to edge information or the like or by dividing it into regions having another shape.

Second Embodiment

FIGS. 19 to 24 relate to a second embodiment of the present invention. Description will be omitted for the portions having the same configuration as those of the first embodiment. Also, the same reference numerals are used for the same constituent elements as those of the first embodiment, and the description will be omitted. Moreover, the configuration of the capsule-type endoscope device 1 used in the second embodiment is the same as that of the first embodiment. The image processing operation in the second embodiment is carried out as processing at the control portion 9a provided at the terminal body 9.

Figure 19:
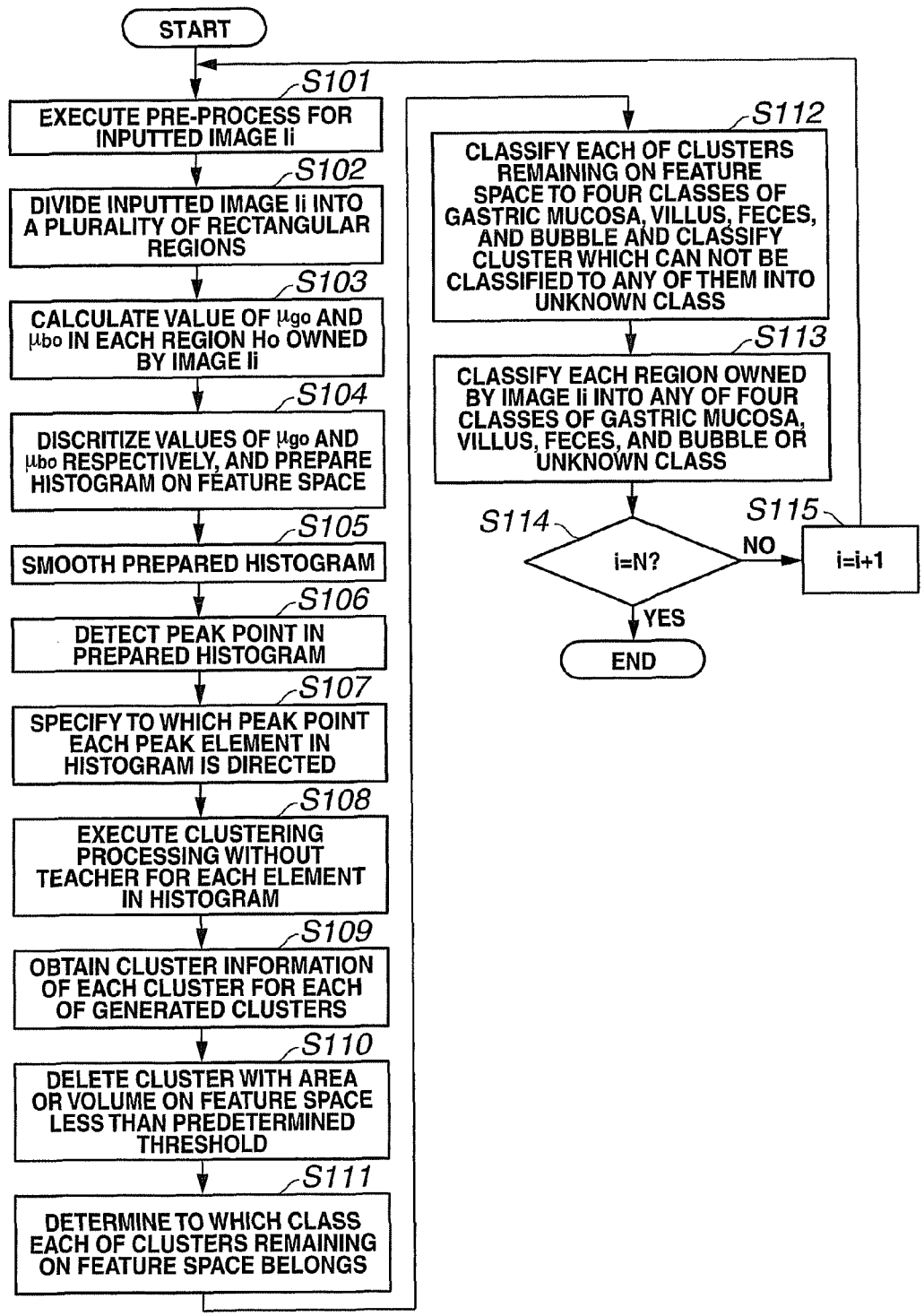
FIG. 19 is a flowchart showing an image processing operation according to a second embodiment.
Figure 20:
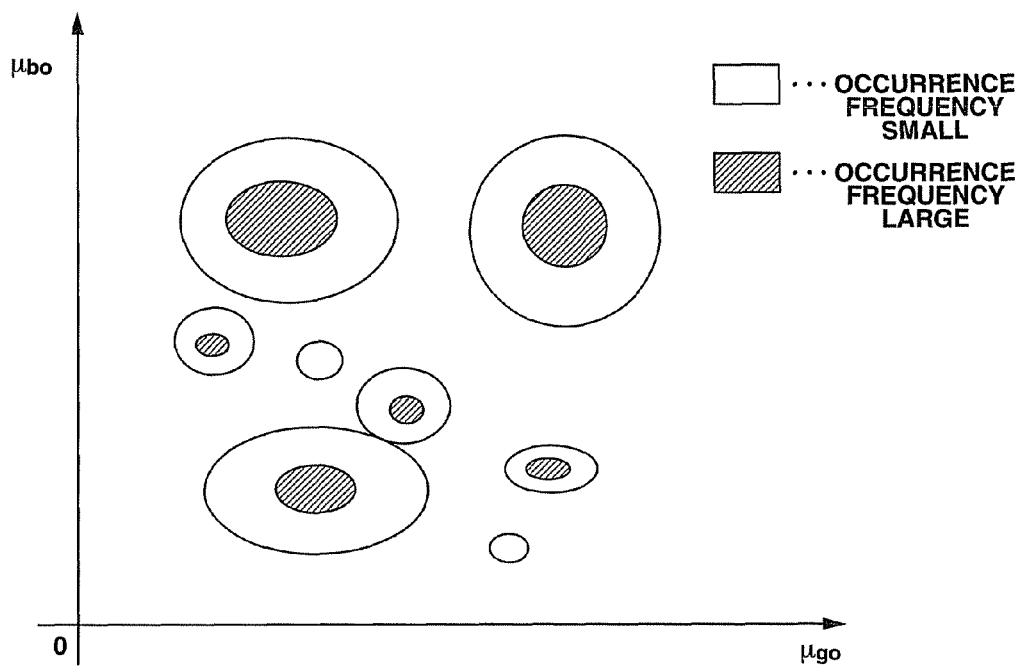
FIG. 20 is a diagram showing an example of a histogram in a feature space generated by processing executed by the control portion in the second embodiment.
Figure 21:
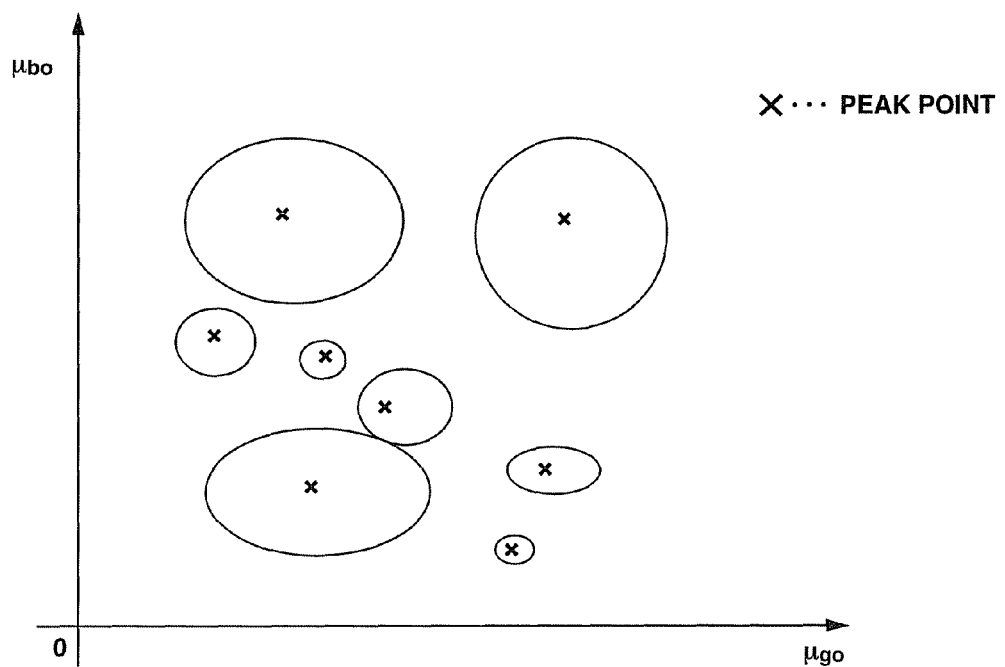
FIG. 21 is a diagram showing an example of clusters in the feature space generated by processing executed by the control portion in the second embodiment.
Figure 22:
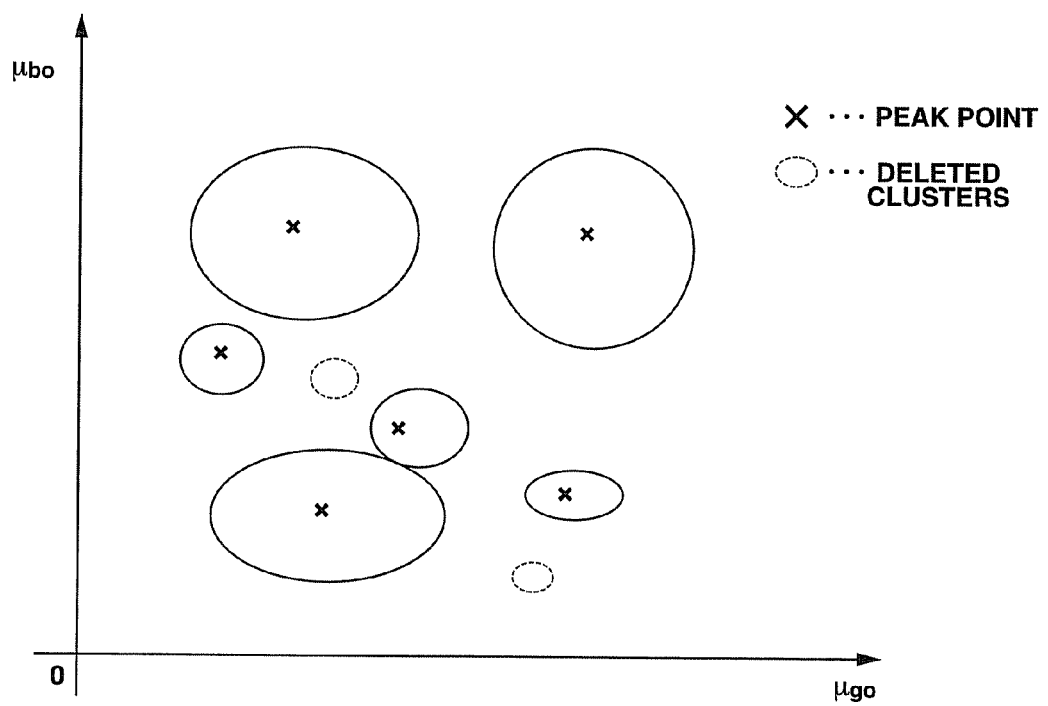
FIG. 22 is a diagram showing a state where the cluster with an area or volume in the feature space less than a threshold value in the clusters shown in FIG. 21 is deleted.
Figure 23:
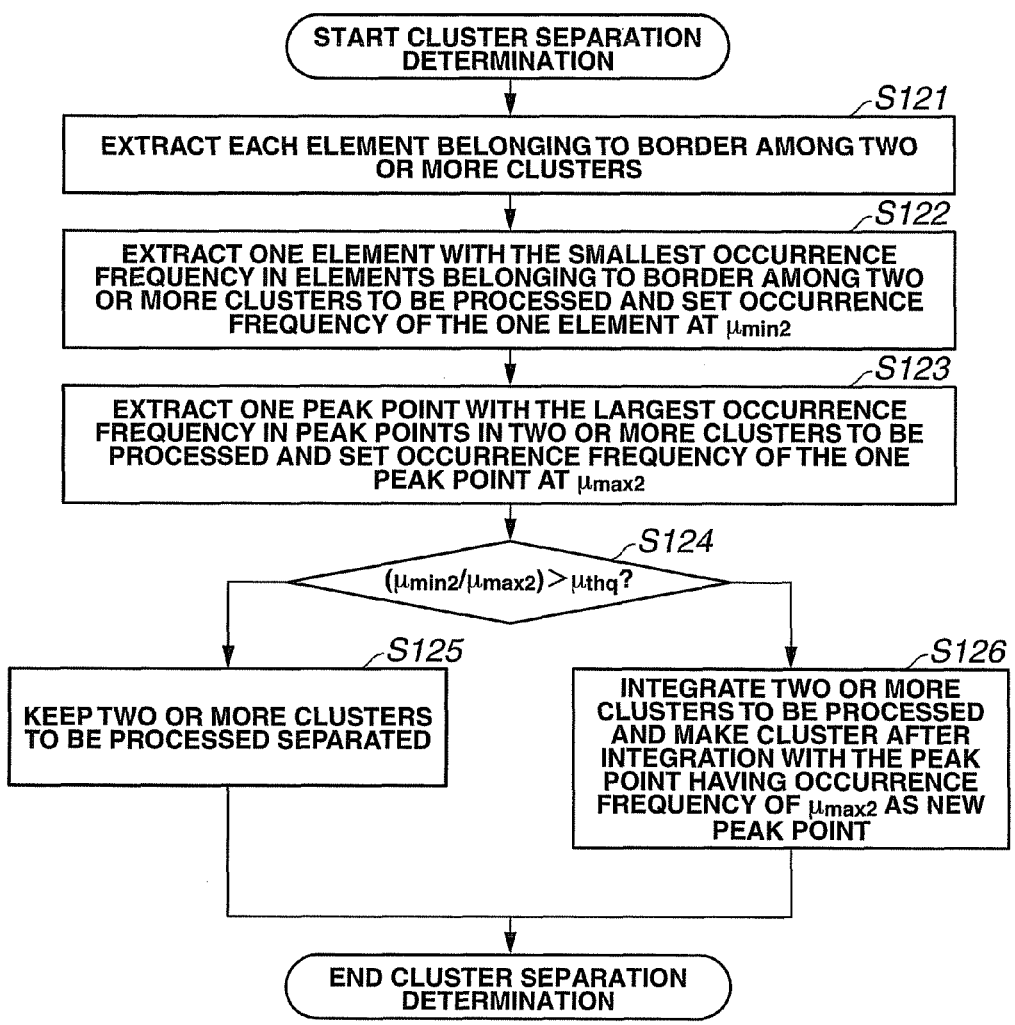
FIG. 23 is a flowchart showing an example of processing for integration or separation determination of two or more bordering clusters, which is processing executed by the control portion.
Figure 24:
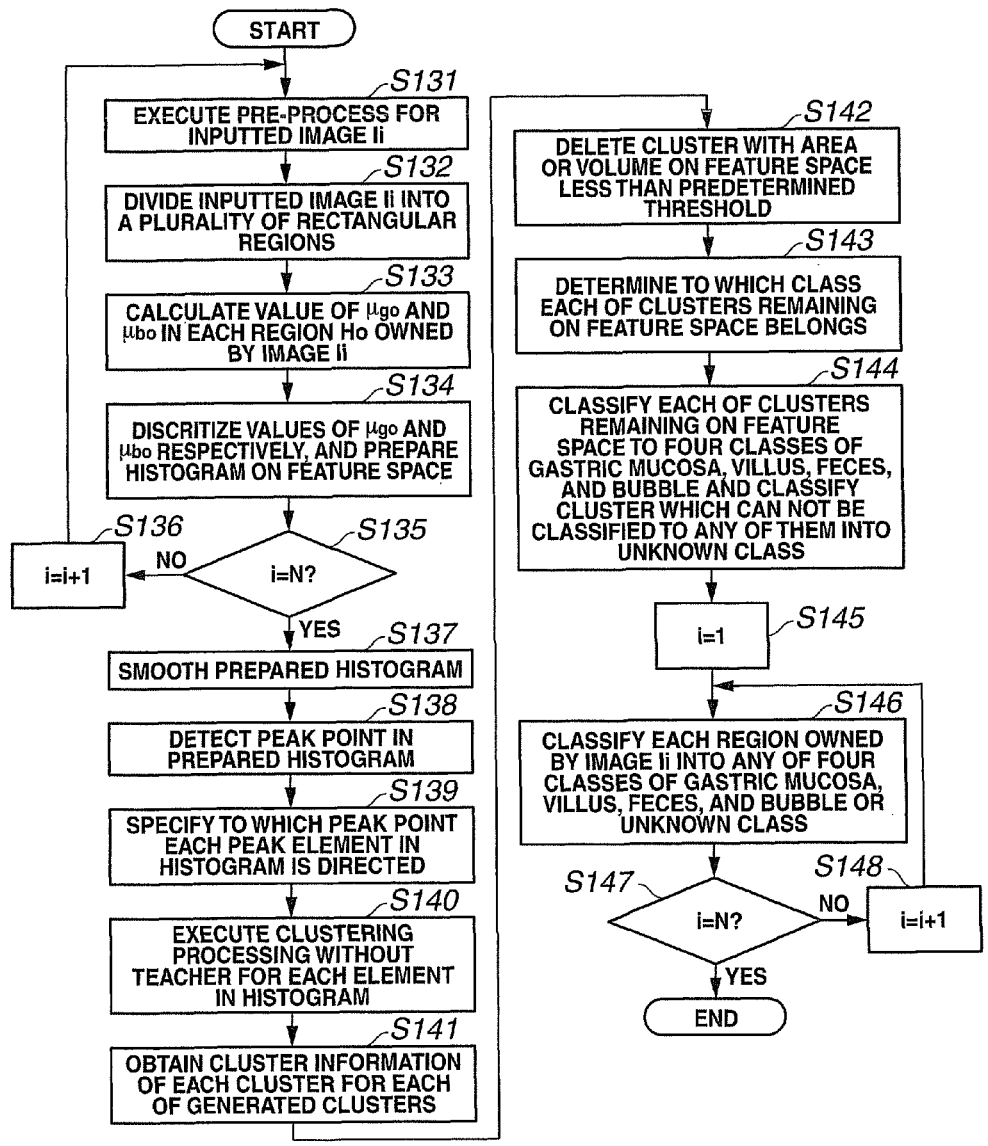
FIG. 24 is a flowchart showing a variation of the image processing operation shown in FIG. 19.

FIG. 19 is a flowchart showing the image processing operation according to the second embodiment. FIG. 20 is a diagram showing an example of a histogram in a feature space generated by processing executed by the control portion in the second embodiment. FIG. 21 is a diagram showing an example of clusters in the feature space generated by processing executed by the control portion in the second embodiment. FIG. 22 is a diagram showing a state where the cluster with an area or volume in the feature space less than a threshold value in the clusters shown in FIG. 21 is deleted. FIG. 23 is a flowchart showing an example of processing for integration or separation determination of two or more bordering clusters, which is processing executed by the control portion. FIG. 24 is a flowchart showing a variation of the image processing operation shown in FIG. 19.

The image processing operation in the image processing device in the second embodiment will be described.

In the second embodiment, as with the first embodiment, an image of the inside of a body cavity picked up by the capsule-type endoscope 3 is comprised by the number of dots in the x-axis direction ISX×the number of dots in the y-axis direction ISY (a value satisfying $1 \leq ISX$, $1 \leq ISY$ and ISX=300, ISY=300, for example), three planes of R (red), G (green), B (blue), and each pixel in each plane takes a value of 8 bits each as an RGB value, which is a density value, that is, a value from 0 to 255. Also, in the second embodiment of the present invention as in the first embodiment, the i-th image in N pieces of images ($1 \leq N$) picked up continuously in a time series is indicated as Ii ($1 \leq i \leq N$). Moreover, in the second embodiment, a w-th pixel ($1 \leq w \leq ISX \times ISY$) in each plane of the image Ii is indicated as riw, giw and biw, respectively.

Also, the image processing operation in the image processing device in this embodiment is, as in the first embodiment, carried out as processing in the above-mentioned control portion 9a provided at the terminal body 9 of the terminal device 7.

First, at the control portion 9a, noise elimination by median filtering and inverse γ correction, for example, are carried out as pre-process for each plane of Ri, Gi and Bi constituting the inputted i-th image Ii and at the same time, in order to eliminate a halation pixel and a dark part pixel, they are detected by processing based on a threshold value (Step S101 in FIG. 19). The processing based on the threshold value is carried out as processing to determine as the dark part pixel if all the density values of riw, giw and biw are 10 or less or as the halation pixel if all the density values of riw, giw and biw are 230 or more, for example.

After that, the control portion 9a divides the inputted image Ii into a plurality of rectangular regions made of 8×8, for example (Step S102 in FIG. 19). In the subsequent description, one region in the rectangular regions divided at the control portion 9a is indicated as Ho (o is an integer of 1 or more).

Then, the control portion 9a calculates two feature values indicating chromaticity of the image, which are values based on a ratio of the RGB value of each pixel in each one region Ho of the image Ii and made of an average value of giw/riw (hereinafter referred to as μgo) and an average value of biw/giw (hereinafter referred to as μbo) (Step S103 in FIG. 19).

Moreover, the control portion 9a discritizes the feature values μgo and μbo obtained in each of the regions Ho, respectively, and prepares a histogram in a feature space based on the occurrence frequency of the discritized feature values μgo and μbo (Step S104 in FIG. 19). Specifically, the control portion 9a makes all the values of μgo and μbo at 1 or more as 1 and handles them as they take values from 0 to 1, respectively, and moreover, values obtained by multiplying the feature values μgo and μbo as the values from 0 to 1 by 80 are rounded off to integer values and discritization and creation of a histogram are performed. When more than the predetermined number of halation pixels and dark part pixels are detected in the one region Ho included in the image Ii, the control portion 9a may eliminate the one region Ho from application of the subsequent processing.

The control portion 9a applies an average-value filter of a predetermined size, for example, to the discritized feature values μgo and μbo so as to smooth the histogram (Step S105 FIG. 19). The histogram prepared by the above processing of the control portion 9a is as shown in FIG. 20, for example.

Next, in the histogram prepared by executing the above-mentioned processing for the inputted image Ii, the control portion 9a detects an element with the maximum occurrence frequency (μgo, μbo), that is, a peak point (Step S106 in FIG. 19). Specifically, the control portion 9a extracts nine elements consisting of one element and eight elements neighboring the one element in the prepared histogram and then, detects the element with the largest occurrence frequency as the peak point in the extracted nine elements.

The control portion 9a specifies to which peak point among the detected peak points each element other than (μgo, μbo) =(0, 0) is directed in the prepared histogram by using a Valley-Seeking method, for example, as an analysis method on the basis of a gradient vector (Step S107 in FIG. 19). And the control portion 9a carries out clustering processing without a teacher for each element in the histogram, which is processing to consider the elements having the gradient vector directed to the same peak point as elements belonging to the same cluster (Step S108 in FIG. 19). Each cluster prepared by the clustering processing without a teacher by the control portion 9a is as shown in FIG. 21, for example.

If the control portion 9a detects that two or more clusters are bordered in the above clustering processing without a teacher, it may further carry out processing of integration or separation determination of the two or more clusters as described below.

In that case, it is determined that the two or more clusters are bordered by extracting the element including two or more clusters in the nine elements including the eight neighboring elements in each prepared cluster, that is, by extracting the elements belonging to the border of two or more clusters (Step S121 in FIG. 23). Moreover, the control portion 9a extracts one element with the smallest occurrence frequency in the elements belonging to the border of the two or more clusters to be processed and sets the occurrence frequency in the one element at μmin2 (Step S122 in FIG. 23). Also, the control portion 9a extracts one peak point with the largest occurrence frequency in the peak points in the two or more clusters to be processed and sets the occurrence frequency in the one peak point at μmax2 (Step S123 in FIG. 23).

After extracting μmin2 and μmax2, the control portion 9a compares the value of μmin2/μmax2 and a threshold value μthq. When the control portion 9a detects that the value of μmin2/μmax2 is larger than the threshold value μthq (Step S124 in FIG. 23), the two or more clusters to be processed are determined as separate clusters and the two or more clusters are kept separated (Step S25 in FIG. 15). Also, when the control portion 9a detects that the value of μmin2/μmax2 is smaller than the threshold value μthq (Step S24 in FIG. 15), it is determined that the two or more clusters to be processed belong to the same cluster and the two or more clusters are integrated and a cluster after integration with the peak point of the occurrence frequency μmax2 made as a new peak point is prepared (Step S26 in FIG. 15). The above threshold value μthq is 0.1, for example, in the second embodiment.

After the above clustering processing without a teacher (processing shown at step S108 in FIG. 19), the control portion 9a obtains cluster information of each cluster for each generated cluster (Step S109 in FIG. 19). The cluster information obtained by the control portion 9a is information such as a cluster number, an element to be the peak point of each cluster, an area and a volume of each cluster in the feature space, an average value vector of the feature values μgo and μbo in each cluster, for example.

After that, the control portion 9a deletes the clusters with the area or volume in the feature space less than a predetermined threshold value on the basis of the obtained cluster information as shown in FIG. 22 (Step S110 in FIG. 19).

Moreover, by using a classifier of linear discrimination function or function based on Bayes' theorem, for example, prepared from the average value vector of the feature values μgo and μbo in each cluster remaining in the feature space and a training data set, the control portion 9a determines to which class each cluster remaining in the feature space belongs (Step S111 in FIG. 19). In the second embodiment, they shall be four classes consisting of gastric mucosa, villus, feces and bubble. Also, in the second embodiment, the training data set shall be a plurality of images constituting training data of the four classes.

The control portion 9a classifies each cluster remaining in the feature space to the four classes of gastric mucosa, villus, feces and bubble and classifies a cluster which can not be classified into any of the four classes into an unknown class (Step S112 in FIG. 19).

A specific example of processing shown in Step S111 and step S112 in FIG. 19 will be described below in detail. The control portion 9a is supposed to carry out each of the processing described below for all the clusters remaining in the feature space.

In the identification and classification of the above four classes, a prior probability that one class ωa (a=1, 2, ..., C, C indicates the class number) occurs is set as P(ωa), a characteristic vector determined from the feature values μgo and μbo in each cluster remaining in the feature space as x, a probability density function on the basis of the occurrence probability of the characteristic vector x from all the classes as p(x), and a conditional probability density (multivariate normal probability density) function on the basis of an occurrence probability of the characteristic vector x from the one class ωa as p(x|ωa), a calculation formula to calculate a posterior probability P(ωa|x) that an occurring characteristic vector x belongs to one class ωa is shown as the following expression (5):

$$P(\omega a|x)=p(x|\omega a)P(\omega a)/p(x) \tag{5}$$

The conditional probability density function p(x|ωa) and the probability density function p(x) are shown by the following equation (6) and equation (7):

$$p(x|\omega a) = (1/((2\pi)^{d/2}|\Sigma a|^{1/2}))\exp[(-1/2)(\underline{x}-\underline{\mu a})^t \Sigma a^{-1}(\underline{x}-\underline{\mu a})] \tag{6}$$

$$p(x) = \sum_{a=1}^{C} p(x|\omega a)P(\omega a) \tag{7}$$

In the above equations (6) and (7), d indicates the number of dimensions in the same number as that of the feature value of x, μa and Σa indicate an average vector of the characteristic vector x in the class ωa and a variance-covariance matrix in the one class ωa. Also, $(x-\mu a)^t$ indicates a transposed matrix of (x-μa), |Σa| indicates a determinant of Σa, and $\Sigma a^{-1}$ indicates an inverse matrix of Σa. Moreover, in order to facilitate the description, the prior probability P(ωa) is presumed to take an equal value in all the classes, and the probability density function p(x) is expressed by the above equation (7) as a function common to all the classes.

Together with the statistical classifier on the basis of the above-mentioned Bays' theorem, the average vector μa and the variance-covariance matrix Σa are elements constituting a population parameter in one class ωa, and at the stage before the first image I1 is inputted into the terminal device 7, it is calculated for each class in advance from the characteristic vector x determined every time in each of the regions of the image on the basis of a plurality of images constituting the training data of the four classes consisting of gastric mucosa, villus, feces and bubble and then, recorded in the terminal device 7 as an initial value, respectively. At this time, the control portion 9a may estimate the parameter by adding the characteristic vector of each class in the image Ii to the characteristic vector in the training data of each class.

The average vector μa is comprised by average values of the two feature values owned by the characteristic vector x and is a vector having the same number of dimensions as that of the characteristic vector x. That is, when the characteristic vector x is represented as x=(μgo, μbo), the average vector μa shall be represented as μa=(μ(μgo), μ(μbo)) using μ(μgo) and μ(μbo), which are average values of the two feature values owned by the characteristic vector x, respectively. Also, the variance-covariance matrix Σa is a matrix indicating variation and wideness of distribution of the characteristic vector x belonging to one class ωa and is represented as d×d matrix to the number of dimensions d, which is equal to the number of feature values of the characteristic vector x.

The control portion 9a calculates the posterior probability P(ω1|x) that an occurring characteristic vector x belongs to one class ω1, the posterior probability P(ω2|x) that the occurring characteristic vector x belongs to one class ω2, the posterior probability P(ω3|x) that the occurring characteristic vector x belongs to one class ω3, and the posterior probability P(ω4|x) that the occurring characteristic vector x belongs to one class ω4, respectively, using the equations (5) to (7) on the basis of Bays' theorem. And the control portion 9a identifies that the characteristic vector x belongs to the class ωa giving the largest posterior probability P1(ωa|x), classifies one cluster where the characteristic vector x occurred into the class ωa on the basis of the identification result and calculates a value of the probability density function p1(x|ωa) giving the largest posterior probability P1(ωa|x).

In order to determine if the classification result of the one cluster classified into the class ωa is accurate or not in the processing so far, the control portion 9a further executes processing on the basis of the distance from the average value, that is, processing on the basis of the threshold value to the value of the probability density function p1(x|ωa) giving the largest posterior probability P1(ωa|x).

Specifically, first, in the average values of each of the two feature values owned by the average vector μa, for the average value μ(μgo) of the feature value μgo, for example, the threshold vector xb1 including a value to which a product of the standard deviation σ(μgo) of the feature value μgo and a multiplier coefficient α as a predetermined constant is added is determined This threshold vector xb1 is expressed as the following equation (8), for example, and in this embodiment, the value of the multiplier coefficient α shall be 1.5:

$$xb1=(\mu(\mu go)+\alpha\times\sigma(\mu go),\mu bo) \tag{8}$$

When the threshold vector xb1 is determined by the above equation (8), the control portion 9a substitutes the threshold vector xb1 for x of the above equation (5), the equation (6) and the equation (7) so as to calculate the value of the probability density function p(xb1|ωa) as a threshold value of the class ωa to which one cluster is classified.

When the control portion 9a detects that the value of p1(x|ωa) is larger than the value of p(xb1|ωa), it determines that the classification result that the one cluster is classified into the class ωa in the above processing is accurate.

On the other hand, when the control portion 9a detects that the value of p1(x|ωa) is smaller than the value of p(xb1|ωa), it determines that the classification result that the one cluster is classified into the class ωa in the above processing is not accurate, and the one cluster is classified into an unknown class.

The control portion 9a classifies each region into any of the above-mentioned four classes and the unknown class on the basis of the classification result of the element owned by each cluster in the feature space and each cluster obtained by the processing so far and the feature values μgo and μbo calculated in each region owned by the image Ii (Step S113 in FIG. 19). Specifically, the control portion 9a classifies each region Ho into the same class as the class into which a cluster is classified where the values of the feature values μgo and μbo calculated and discritized in each region Ho belong.

When there is an element not belonging to any class in the feature space, the control portion 9a classifies the region in the regions owned by the image Ii where the feature value corresponding to the element is calculated into the unknown class.

When the processing shown in Step S101 to Step S113 in FIG. 19 has not been completed for all the N pieces of inputted images (Step S114 in FIG. 19), the control portion 9a adds 1 to the image number i (Step S115 in FIG. 19) and continuously carries out the processing shown in Step S101 to Step S114 in FIG. 19 for the subsequent image. Also, when the processing shown in Step S101 to Step S113 in FIG. 19 has been completed for all the N pieces of inputted images (Step S114 in FIG. 19), the control portion 9a ends the series of processing.

By executing the processing shown in Step S101 to Step S115 in FIG. 19 as mentioned above, the control portion 9a can classify images picked up by the capsule-type endoscope 3 with high accuracy and at high speed.

In the above-mentioned processing, the processing shown in Step S104 in FIG. 19, that is, processing to prepare a histogram in the feature space is not limited to execution per single image but it may be carried out for N pieces of images.

In that case, first, the control portion 9a executes the same processing as that shown in the above-mentioned Step S101, Step S102 and Step S103 in FIG. 19 (Step S131 in FIG. 24, Step S132 in FIG. 24 and Step S133 in FIG. 24). That is, the control portion 9a executes pre-process and region division of the inputted image Ii and calculates the feature values μgo and μbo in each region Ho obtained by dividing the image Ii.

After that, the control portion 9a discritizes the feature values μgo and μbo obtained in each of the regions Ho, respectively, as substantially the same processing as that shown in Step S104 in FIG. 19 and prepares a histogram in a feature space based on the occurrence frequency of the discritized feature values μgo and μbo (Step S134 in FIG. 24).

When the processing shown in Step S131 to Step S134 in FIG. 24 has not been completed (Step S135 in FIG. 24) for all the N pieces of inputted images, the control portion 9a adds 1 to the image number i (Step S136 in FIG. 24) and continuously carries out the processing shown in Step S131 to Step S135 in FIG. 24 for the subsequent image.

When the processing shown in Step S131 to Step S134 in FIG. 24 has been completed (Step S135 in FIG. 24) for all the N pieces of inputted images, the control portion 9a carries out the same processing as the processing shown in step S105 to Step S112 in FIG. 19 (Step S137 to Step S144 in FIG. 24). That is, the control portion 9a carries out the clustering processing without a teacher on the basis of the prepared histogram and classifies each obtained cluster into four classes of gastric mucosa, villus, feces and bubble and a cluster which can not be classified into any of the four classes into the unknown class. The control portion 9a obtains the feature value distribution information showing the distribution state per class of the feature values μgo and μbo included in the cluster occurring in the feature space in the processing shown in Step S144 in FIG. 24, that is, the processing to classify each cluster remaining in the feature space into the four classes of gastric mucosa, villus, feces and bubble and to classify a cluster which can not be classified into any of the four classes into the unknown class.

After that, the control portion 9a executes processing for the first image I1 to classify each region owned by the image I1 into any of the four classes of gastric mucosa, villus, feces and bubble and the unknown class (Step S145 and Step S146 in FIG. 24).

When the processing shown in Step S146 in FIG. 24 has not been completed (Step S147 in FIG. 24) for all the N pieces of inputted images, the control portion 9a adds 1 to the image number i (Step S148 in FIG. 24) and continuously carries out the processing shown in Step S146 to Step S147 in FIG. 24 for the subsequent image. When the processing shown in Step S146 in FIG. 24 has been completed (Step S147 in FIG. 24), the control portion 9a ends the series of processing from Step S131 to Step S148 in FIG. 24.

In addition to the feature value distribution information obtained by executing the processing shown in step S144 in FIG. 24, the control portion 9a may make determination of an imaged portion per image by using a determination standard which determines the image in which the region Ho classified into a predetermined class holds a predetermined proportion or more in the image Ii in the images I1 to IN as the image in which a predetermined organ is imaged, for example. Specifically, the control portion 9a may determine that an image in which the region Ho classified into the feces class holds 10% or more in the image Ii in images I1 to IN as an image in which large intestine is imaged. The above processing of the imaged portion determination carried out by the control portion 9a may be executed along with the processing in Step S112 in FIG. 19.

By executing the processing shown in Step S131 to Step S148 in FIG. 24 as mentioned above, the control portion 9a can classify images picked up by the capsule-type endoscope 3 with higher accuracy as compared with the processing shown in Step S101 to Step S115 in FIG. 19.

The control portion 9a may carry out the following processing using a statistical classifier or the like configured on the basis of the feature value distribution information obtained by carrying out the processing shown in Step S114 in FIG. 24, for example, as the processing to classify each region owned by the image Ii with higher accuracy.

In that case, after the processing shown in Step S144 in FIG. 24, the control portion 9a calculates the average value vector and variance-covariance matrix as a criterion of classification on the basis of the feature value distribution information obtained in the processing shown in step S144 in FIG. 24 and constitutes the statistical classifier using the average value vector and variance-covariance matrix.

Moreover, on the basis of the statistical classifier constituted by the above processing and the feature values μgo and μbo calculated in each region owned by the image Ii, the control portion 9a classifies the region into any of the above-mentioned four classes and the unknown class.

The above image processing method is not limited only to an image picked up by the capsule-type endoscope but may be applied to an image picked up by an endoscope which can be inserted into a living body and having an imaging function.

As mentioned above, according to the image processing method in this embodiment, images can be classified with accuracy and at high speed for each target to be imaged and moreover, an imaged organ can be identified on the basis of the classification result. As a result, observation effects by users can be improved.

Third Embodiment

FIGS. 25 to 30 relate to a third embodiment of the present invention. Description will be omitted for the portions having the same configuration as those of the first embodiment and the second embodiment. Also, the same reference numerals are used for the same constituent elements as those of the first embodiment and the second embodiment, and the description will be omitted. Moreover, the configuration of the capsule-type endoscope device 1 used in the third embodiment is the same as that of the first embodiment and the second embodiment. The image processing operation in the third embodiment is carried out as processing at the control portion 9a provided at the terminal body 9.

Figure 25:
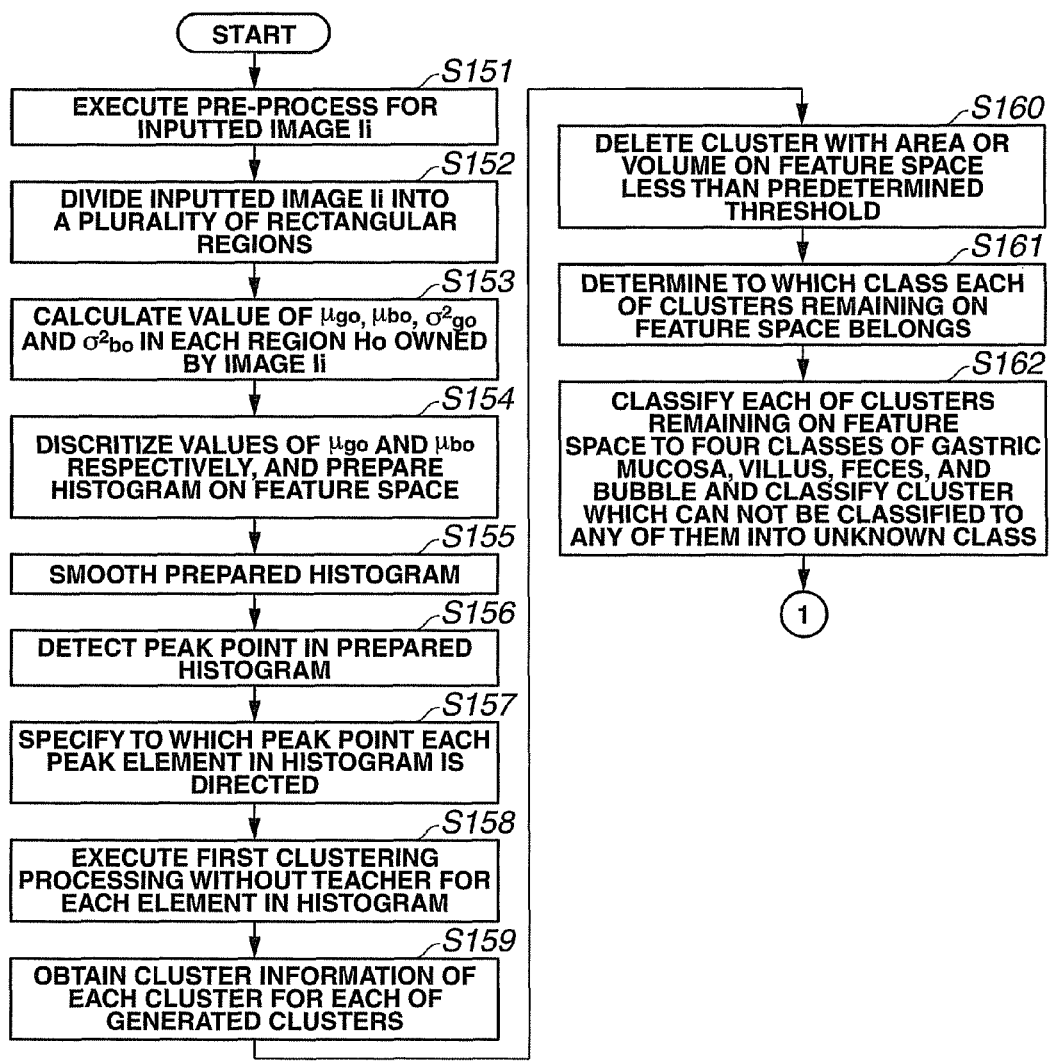
FIG. 25 is a flowchart showing an image processing operation according to a third embodiment.
Figure 26:
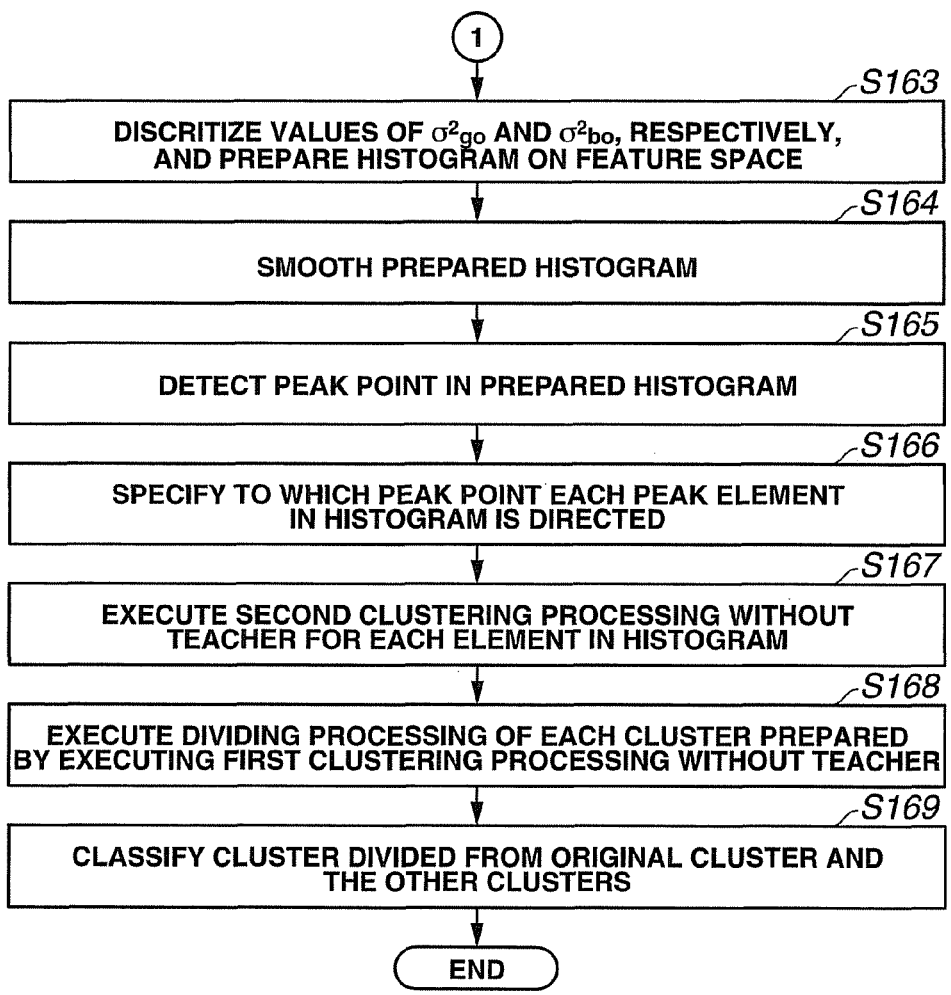
FIG. 26 is a flowchart showing an image processing operation executed subsequent to the processing shown in FIG. 25.
Figure 27:
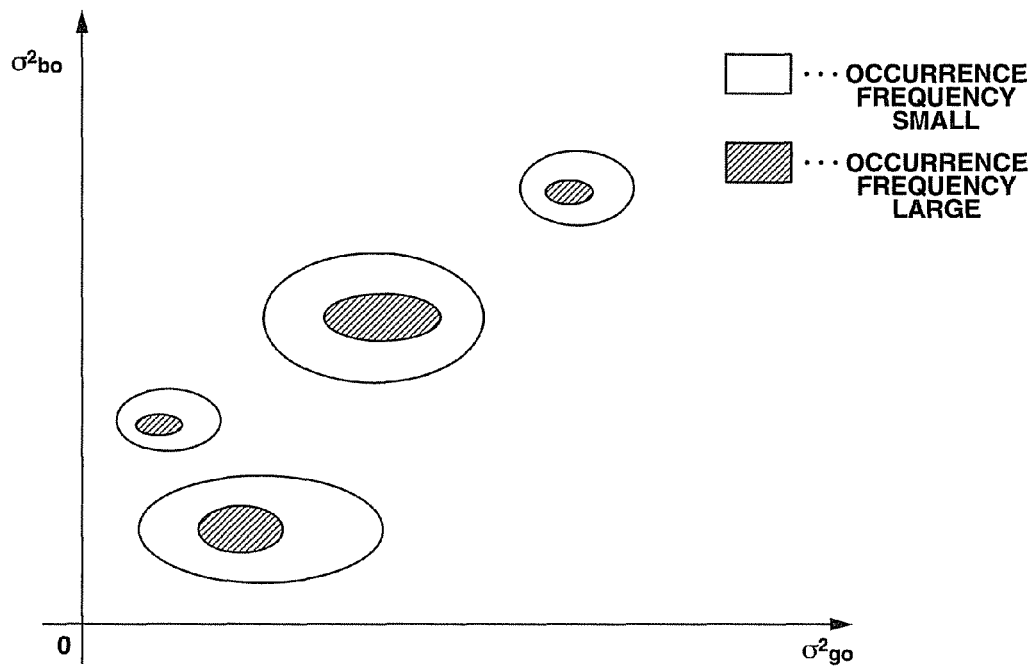
FIG. 27 is a diagram showing an example of a histogram in the feature space generated by processing executed by the control portion in the third embodiment.
Figure 28:
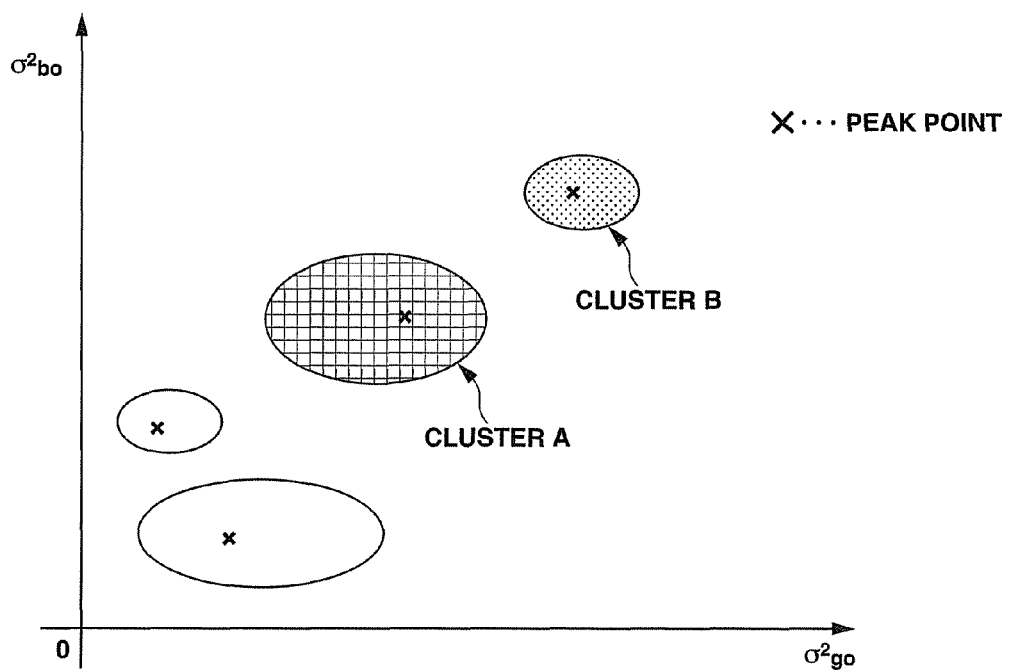
FIG. 28 is a diagram showing an example of the cluster in the feature space generated by a second clustering processing without a teacher executed by the control portion in the third embodiment.
Figure 29:
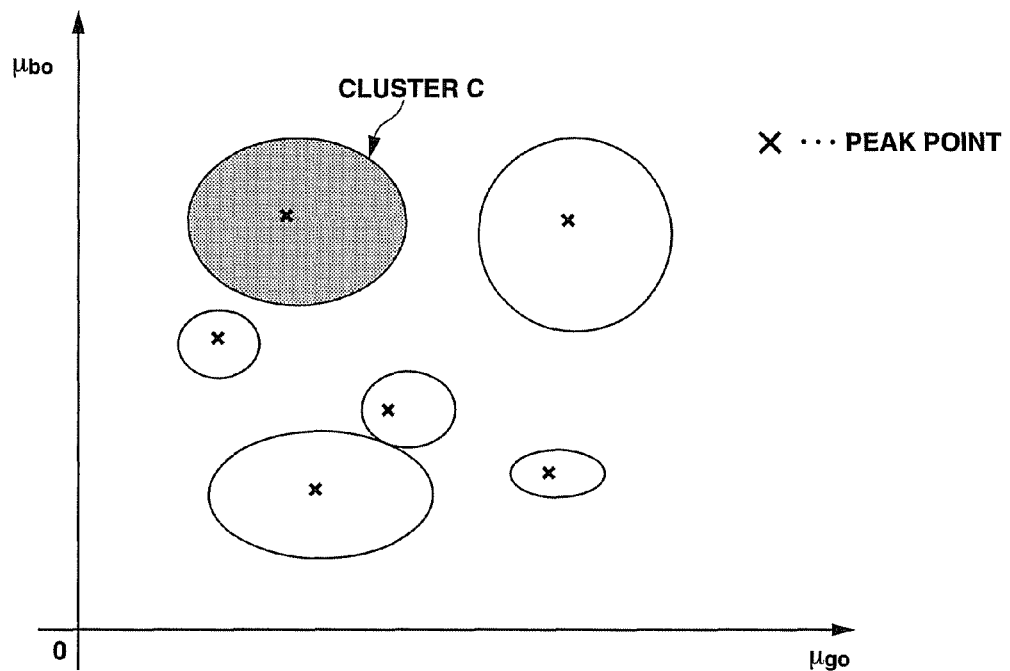
FIG. 29 is a diagram showing an example of the cluster in the feature space generated by a first clustering processing without a teacher executed by the control portion in the third embodiment.
Figure 30:
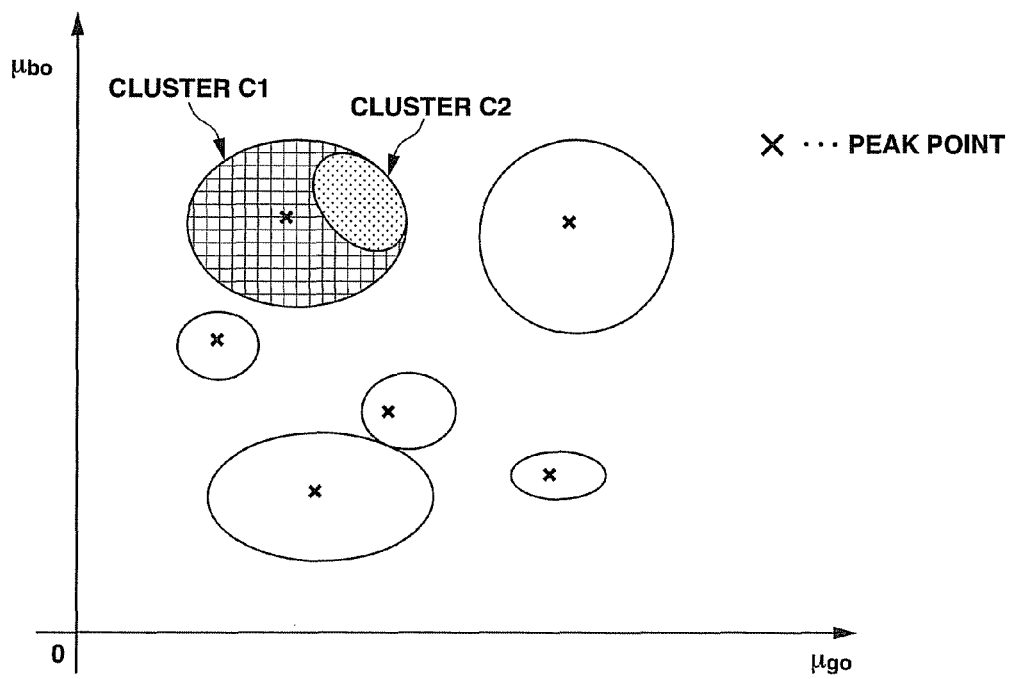
FIG. 30 is a diagram showing a state where the cluster C shown in FIG. 29 is divided into a cluster C1 and a cluster C2 by the dividing processing executed by the control portion in the third embodiment.

FIG. 25 is a flowchart showing an image processing operation according to the third embodiment. FIG. 26 is a flowchart showing an image processing operation executed subsequent to the processing shown in FIG. 25. FIG. 27 is a diagram showing an example of a histogram in the feature space generated by processing executed by the control portion in the third embodiment. FIG. 28 is a diagram showing an example of the cluster in the feature space generated by a second clustering processing without a teacher executed by the control portion in the third embodiment. FIG. 29 is a diagram showing an example of the cluster in the feature space generated by a first clustering processing without a teacher executed by the control portion in the third embodiment. FIG. 30 is a diagram showing a state where the cluster C shown in FIG. 29 is divided into a cluster C1 and a cluster C2 by the dividing processing executed by the control portion in the third embodiment.

The image processing operation in the image processing device in the third embodiment will be described.

First, at the control portion 9a, noise elimination by median filtering and inverse γ correction, for example, are carried out as pre-process for each plane of Ri, Gi and Bi constituting the inputted i-th image Ii and at the same time, in order to eliminate a halation pixel and a dark part pixel, they are detected by processing based on a threshold value (Step S151 in FIG. 25). The processing based on the threshold value is carried out as processing to determine as the dark part pixel if all the density values of riw, giw and biw are 10 or less or as the halation pixel if all the density values of riw, giw and biw are 230 or more, for example.

After that, the control portion 9a divides the inputted image Ii into a plurality of rectangular regions made of 8×8, for example (Step S152 in FIG. 25).

Then, the control portion 9a calculates two feature values indicating chromaticity of the image, which are values made of μgo and μbo based on a ratio of the RGB value of each pixel in each one region Ho of the image Ii and two feature values indicating variation in the chromaticity of the image, which are values made of variance of giw/riw (hereinafter referred to as $\sigma^2 go$) and variance of biw/giw (hereinafter referred to as $\sigma^2 bo$) (Step S153 in FIG. 25). The control portion 9a may calculate a standard deviation of giw/riw, σgo and the standard deviation of biw/giw, σbo, for example, not limited to calculation of $\sigma^2 go$ and $\sigma^2 bo$ as the feature values indicating the variation of the chromaticity of the image.

The control portion 9a discritizes the feature values μgo and μbo obtained in each of the regions Ho, respectively, and prepares a histogram in a feature space based on the occurrence frequency of the discritized feature values μgo and μbo (Step S154 in FIG. 25).

The control portion 9a applies an average-value filter of a predetermined size, for example, to the discritized feature values μgo and μbo so as to smooth the histogram (Step S155 FIG. 25). The histogram prepared by the above processing of the control portion 9a is substantially similar to the one shown in FIG. 20, for example.

Next, in the histogram prepared by executing the above-mentioned processing for the inputted image Ii, the control portion 9a detects an element with the maximum occurrence frequency (μgo, μbo), that is, a peak point (Step S156 in FIG. 25). Specifically, the control portion 9a extracts nine elements consisting of one element and eight elements neighboring the one element in the prepared histogram and then, detects the element with the largest occurrence frequency in the extracted nine elements as a peak point.

The control portion 9a specifies to which peak point among the detected peak points each element other than (μgo, μbo) =(0, 0) is directed in the prepared histogram by using a Valley-Seeking method, for example, as an analysis method on the basis of a gradient vector (Step S157 in FIG. 25). And the control portion 9a carries out first clustering processing without a teacher for each element (μgo, μbo) in the histogram, which is processing to consider the elements having the gradient vector directed to the same peak point as elements belonging to the same cluster (Step S158 in FIG. 25). Each cluster prepared by the first clustering processing without a teacher by the control portion 9a is substantially similar to the one shown in FIG. 21, for example.

After the first clustering processing without a teacher, the control portion 9a obtains cluster information of each cluster for each of the generated clusters (Step S159 in FIG. 25). In the processing shown in Step S159 in FIG. 25, the cluster information obtained by the control portion 9a is information such as a cluster number, an element to be the peak point of each cluster, an area and a volume of each cluster in the feature space, an average value vector of the feature values μgo and μbo in each cluster, for example.

After that, the control portion 9a deletes the clusters with the area or volume in the feature space less than a predetermined threshold value on the basis of the obtained cluster information (Step S160 in FIG. 25).

Moreover, by using a classifier of linear discrimination function or function based on Bayes' theorem, for example, prepared from the average value vector of the feature values μgo and μbo in each cluster remaining in the feature space and a training data set, the control portion 9a determines to which class each cluster remaining in the feature space belongs (Step S161 in FIG. 25). In this embodiment, they shall be four classes consisting of gastric mucosa, villus, feces and bubble. Also, in this embodiment, the training data set shall be a plurality of images constituting training data of the four classes.

The control portion 9a classifies each cluster remaining in the feature space into the four classes of gastric mucosa, villus, feces and bubble and classifies a cluster which can not be classified into any of the four classes into an unknown class (Step S162 in FIG. 25).

The processing in Step S161 and S162 in FIG. 25 in the present embodiment applies substantially the same processing as that shown in Step S111 and Step S112 in FIG. 19 described in the second embodiment.

Also, the control portion 9a discritizes each of the feature values $\sigma^2 go$ and $\sigma^2 bo$ obtained in each region Ho and prepares a histogram in the feature space on the basis of the occurrence frequency of the discritized feature values $\sigma^2 go$ and $\sigma^2 bo$ (Step S163 in FIG. 26).

The control portion 9a applies an average-value filter of a predetermined size, for example, to the discritized feature values $\sigma^2 go$ and $\sigma^2 bo$ so as to smooth the histogram (Step S164 FIG. 26). The histogram prepared by the above processing of the control portion 9a is as shown in FIG. 27, for example.

Next, in the histogram prepared by executing the above-mentioned processing for the inputted image Ii, the control portion 9a detects an element with the maximum occurrence frequency ($\sigma^2 go$, $\sigma^2 bo$), that is, a peak point (Step S165 in FIG. 26). Specifically, the control portion 9a extracts nine elements consisting of one element and eight elements neighboring the one element in the prepared histogram and then, detects the element with the largest occurrence frequency in the extracted nine elements as a peak point.

The control portion 9a specifies to which peak point among the detected peak points each element other than ($\sigma^2 go$, $\sigma^2 bo$) =(0, 0) is directed in the prepared histogram by using a Valley-Seeking method, for example, as an analysis method on the basis of a gradient vector (Step S166 in FIG. 26). And the control portion 9a carries out second clustering processing without a teacher for each element in the histogram for the elements ($\sigma^2 go$, $\sigma^2 bo$) in the histogram, which is processing to consider the elements having the gradient vector directed to the same peak point as elements belonging to the same cluster (Step S167 in FIG. 26). Each cluster prepared by the second clustering processing without a teacher by the control portion 9a is as shown in FIG. 28, for example.

On the basis of the distribution state of each element (μgo and μbo) in each cluster prepared by the first clustering processing without a teacher and the distribution state of each element ($\sigma^2$go, $\sigma^2$bo) in each cluster prepared by the second clustering processing without a teacher, the control portion 9a carries out division processing of each cluster by the first clustering processing without a teacher as described below (Step S168 in FIG. 26).

In the following description, a case is supposed that a cluster A and a cluster B as shown in FIG. 28 are prepared in the feature space indicating variation in chromaticity of the image by the second clustering processing without a teacher and a cluster C as shown in FIG. 29 is prepared in the feature space indicating chromaticity of the image by the first clustering processing without a teacher.

When the control portion 9a detects that $\sigma^2$go1 and $\sigma^2$bo1 calculated as the feature values of one region Ho1 belong to the cluster A, μgo1 and μbo1 calculated as the feature values of the one region Ho1 belong to the cluster C, $\sigma^2$go2 and $\sigma^2$bo2 calculated as the feature values of another region Ho2 belong to the cluster B, and μgo2 and μbo2 calculated as the feature values of the another region Ho2 belong to the cluster C, the control portion 9a determines that the cluster C is a cluster in which elements in two classes are mixed. And the control portion 9a executes processing to divide the original cluster C into one cluster C1 to which μgo1 and μbo1 belong and another cluster C2 to which μgo2 and μbo2 belong on the basis of the detection result as shown in FIG. 30.

After that, using the classifier prepared from the average value vector of the feature values μgo1 and μbo1 and the training data set, the control portion 9a classifies the cluster C1, which is one cluster divided from the original cluster, and using the classifier prepared from the average value vector of the feature values μgo2 and μbo2 and the training data set, the control portion 9a classifies the cluster C2, which is another cluster divided from the original cluster (Step S169 in FIG. 26).

The processing from Step S163 to Step S169 in FIG. 26 may be carried out only for the clusters classified into a specific class such as the gastric mucosa class and the villus class in the processing in Step S161 in FIG. 25, for example.

Also, in the above-mentioned processing, the control portion 9a may carry out the processing from Step S163 to Step S169 in FIG. 26 while omitting the processing in Step S161 and Step S162 in FIG. 25. Specifically, the control portion 9a may classify each cluster prepared by the first clustering processing without a teacher on the basis of the classification result of each cluster prepared by the second clustering processing without a teacher.

The above image processing method is not limited only to an image picked up by the capsule-type endoscope but may be applied to an image picked up by an endoscope which can be inserted into a living body and having an imaging function.

As mentioned above, according to the third embodiment, images can be classified with accuracy and at high speed for each target to be imaged and moreover, observation effects by users can be improved.

Also, according to the third embodiment, in addition to the cluster generation and classification on the basis of color, since cluster generation and classification on the basis of variation in color are carried out at the same time, classification of images where bubbles and villus are imaged with clear structural characteristics can be made with high accuracy.

Moreover, in the second embodiment and the third embodiment of the present invention, the description is made that the control portion 9a carries out a series of processing by dividing the one region Ii into a plurality of rectangular regions with the size of 8×8, but not limited to this, processing may be executed by dividing it into 1×1, that is, per pixel or by dividing it into rectangular regions with another size.

Moreover, in the second embodiment and the third embodiment, description was made that the control portion 9a carries out a series of processing by dividing one image Ii into a plurality of rectangular regions with the size of 8×8, but not limited to this, processing may be executed by dividing it into regions on the basis of the classification result in one image Ii according to edge information or the like or by dividing into regions having another shape.

It is needless to say that the present invention is not limited to the above-mentioned embodiments but various changes and applications can be made in a range not departing from the gist of the invention.

What is claimed is:

1. An image processing device comprising:
an image signal input portion for inputting an image signal of images obtained by medical equipment having an imaging function; an image dividing portion for dividing each of a plurality of images into a plurality of regions, respectively, the plurality of images being representative of the image signal; a feature vector calculation portion for calculating a plurality of feature vectors in each of the plurality of regions; a first cluster classifying portion for generating a first plurality of clusters in a first feature space on the basis of a first feature vector of the plurality of feature vectors and the occurrence frequency of the first feature vector in the plurality of feature vectors and for classifying the first plurality of clusters into any of a plurality of classes, respectively, the first feature space indicating chromaticity of the image; a second cluster classifying portion for generating a second plurality of clusters in a second feature space on the basis of a second feature vector of the plurality of feature vectors and the occurrence frequency of the second feature vector in the plurality of feature vectors and for classifying the second plurality of clusters into any of the plurality of classes, respectively, the second feature space indicating variation in the chromaticity of the image; and a cluster division portion for carrying out division processing such that, when it is detected that the second feature vectors calculated in different regions included in the plurality of regions belong to different clusters respectively in the second plurality of clusters and that the first feature vectors calculated in the different regions included in the plurality of regions belong to one cluster in the first plurality of clusters, the division processing is carried out with respect to the one cluster.

2. An image processing method in an image processing device comprising:
an image dividing step for dividing an image into a plurality of regions, respectively;
a feature vector calculation step for calculating a plurality of feature vectors in each of the plurality of regions;
a first cluster classifying step for generating a first plurality of clusters in a first feature space on the basis of a first feature vector of the plurality of feature vectors and the occurrence frequency of the first feature vector in the plurality of feature vectors and for classifying the first plurality of clusters into any of a plurality of classes, respectively, the first feature space indicating chromaticity of the image;
a second cluster classifying step for generating a second plurality of clusters in a second feature space on the basis of a second feature vector of the plurality of feature vectors and the occurrence frequency of the second feature vector in the plurality of feature values and for classifying the second plurality of clusters into any of the plurality of classes, respectively, the second feature space indicating variation in the chromaticity of the image; and a cluster division step for carrying out division processing such that, when it is detected that the second feature vectors calculated in different regions included in the plurality of regions belong to different clusters respectively in the second plurality of clusters and that the first feature vectors calculated in the different regions included in the plurality of regions belong to one cluster in the first plurality of clusters, the division processing is carried out with respect to the one cluster.

3. An image processing method in an image processing device comprising:

dividing an image obtained by medical equipment into a plurality of regions;

calculating a plurality of feature vectors in each of the plurality of regions;

generating a first plurality of clusters in a first feature space on the basis of a first feature vector and the occurrence frequency of the first feature vector in a plurality of feature vectors and classifying the first plurality of clusters into any one of a plurality of classes, respectively, the first feature space indicating chromaticity of the image;

generating a second plurality of clusters in a second feature space on the basis of a second feature vector and the occurrence frequency of the second feature vector in the plurality of feature vectors and classifying the second plurality of clusters into any of the plurality of classes, respectively, the second feature space indicating chromaticity of the image; and carrying out division processing such that, when it is detected that the second feature vectors calculated in different regions included in the plurality of regions belong to different clusters respectively in the second plurality of clusters and that the first feature vectors calculated in the different regions included in the plurality of regions belong to one cluster in the first plurality of clusters, the division processing is carried out with respect to the one cluster.

\* \* \* \* \*

UNITED STATES PATENT AND TRADEMARK OFFICE
CERTIFICATE OF CORRECTION

| | |
|---|---|
| PATENT NO. | : 8,300,955 B2 |
| APPLICATION NO. | : 13/168510 |
| DATED | : October 30, 2012 |
| INVENTOR(S) | : Hirokazu Nishimura et al. |

Page 1 of 1

It is certified that error appears in the above-identified patent and that said Letters Patent is hereby corrected as shown below:

Column 29, line 3 (claim 2) should read: ture vector in the plurality of feature vectors and for Signed and Sealed this
Second Day of April, 2013

Teresa Stanek Rea
*Acting Director of the United States Patent and Trademark Office*